United States Patent
Weber et al.

(10) Patent No.: US 10,722,395 B2
(45) Date of Patent: Jul. 28, 2020

(54) DEVICES, APPLICATION SYSTEMS AND METHODS WITH LOCALIZED HEAT FLUX ZONES FOR REMOVING HEAT FROM SUBCUTANEOUS LIPID-RICH CELLS

(75) Inventors: Bryan Weber, Livermore, CA (US); Joseph Coakley, Dublin, CA (US); John Potosky, San Jose, CA (US)

(73) Assignee: Zeltiq Aesthetics, Inc., Pleasanton, CA (US)

( * ) Notice: Subject to any disclaimer, the term of this patent is extended or adjusted under 35 U.S.C. 154(b) by 1260 days.

(21) Appl. No.: 13/358,337

(22) Filed: Jan. 25, 2012

(65) Prior Publication Data

US 2012/0239123 A1 Sep. 20, 2012

Related U.S. Application Data

(60) Provisional application No. 61/435,944, filed on Jan. 25, 2011.

(51) Int. Cl.
*A61F 7/00* (2006.01)
*A61F 7/10* (2006.01)
(Continued)

(52) U.S. Cl.
CPC .................. *A61F 7/10* (2013.01); *A61F 7/02* (2013.01); *A61B 2090/0463* (2016.02);
(Continued)

(58) Field of Classification Search
CPC ......... A61B 2019/4063; A61B 18/0218; A61F 2007/0056; A61F 7/10; A61F 207/029;
(Continued)

(56) References Cited

U.S. PATENT DOCUMENTS

| 681,806 A | 9/1901 | Mignault |
| 889,810 A | 6/1908 | Robinson |

(Continued)

FOREIGN PATENT DOCUMENTS

| AU | 2011253768 A1 | 6/2012 |
| CA | 2441489 A1 | 3/2005 |

(Continued)

OTHER PUBLICATIONS

European Search Report, European Patent Application No. EP07761461; Applicant: Zeltiq Aesthetics, Inc., dated Apr. 25, 2012, 9 pages.

(Continued)

*Primary Examiner* — Kaitlyn E Smith
*Assistant Examiner* — Yasamin Ekrami
(74) *Attorney, Agent, or Firm* — Perkins Coie LLP

(57) ABSTRACT

Application systems, disposable interface assemblies and methods for cooling subcutaneous lipid-rich tissue. One embodiment of an application system includes a cooling unit, a cryoprotectant vessel, a contact member and an array of selectively addressable heating elements. The cryoprotectant vessel is configured to contain a fluidic cryoprotectant such that at least a portion of the cryoprotectant is cooled by the cooling unit to a desired base temperature. The contact member is attached to the cryoprotectant vessel and includes a backside in contact with the cryoprotectant and a front side opposite the backside. The contact member is configured to allow the cryoprotectant to flow from the backside to the front side. The array of selectively addressable heating elements is carried by the contact member.

32 Claims, 8 Drawing Sheets

(51) Int. Cl.
  *A61F 7/02* (2006.01)
  *A61B 90/00* (2016.01)
(52) U.S. Cl.
  CPC .............. *A61F 2007/0056* (2013.01); *A61F 2007/0075* (2013.01); *A61F 2007/0095* (2013.01); *A61F 2007/029* (2013.01)
(58) Field of Classification Search
  CPC .............. A61F 2007/0095; A61F 7/00; A61F 2007/0239; A61F 2007/0296; A61F 2007/0298; A61F 2007/0087; A61F 2007/0295; A61F 2007/029; A61F 2007/0075
  See application file for complete search history.

(56) References Cited

U.S. PATENT DOCUMENTS

| | | |
|---|---|---|
| 2,516,491 A | 7/1950 | Swastek |
| 2,521,780 A | 9/1950 | Dodd et al. |
| 3,093,135 A | 6/1963 | Hirschhorn |
| 3,132,688 A | 5/1964 | Nowak |
| 3,133,539 A | 5/1964 | William et al. |
| 3,282,267 A | 11/1966 | Wiliam |
| 3,502,080 A | 3/1970 | Hirschhorn |
| 3,587,577 A | 6/1971 | Smirnov et al. |
| 3,591,645 A | 7/1971 | Selwitz |
| 3,703,897 A | 11/1972 | Mack et al. |
| 3,710,784 A | 1/1973 | Taylor |
| 3,786,814 A | 1/1974 | Armao |
| 3,827,436 A | 8/1974 | Stumpf et al. |
| 3,942,519 A | 3/1976 | Shock |
| 3,948,269 A | 4/1976 | Zimmer |
| 3,986,385 A | 10/1976 | Johnston et al. |
| 4,002,221 A | 1/1977 | Buchalter |
| 4,026,299 A | 5/1977 | Sauder |
| 4,140,130 A | 2/1979 | Storm, III |
| 4,178,429 A | 12/1979 | Scheffer |
| 4,202,336 A | 5/1980 | van Gerven et al. |
| 4,266,043 A | 5/1981 | Fujii et al. |
| 4,381,009 A | 4/1983 | Del Bon et al. |
| 4,396,011 A | 8/1983 | Mack et al. |
| 4,483,341 A | 11/1984 | Witteles |
| 4,528,979 A | 7/1985 | Marchenko et al. |
| 4,531,524 A | 7/1985 | Mioduski |
| 4,548,212 A | 10/1985 | Leung |
| 4,555,313 A | 11/1985 | Duchane et al. |
| 4,585,002 A | 4/1986 | Kissin |
| 4,603,076 A | 7/1986 | Bowditch et al. |
| 4,614,191 A | 9/1986 | Perler |
| 4,644,955 A | 2/1987 | Mioduski |
| 4,664,110 A | 5/1987 | Schanzlin |
| 4,700,701 A | 10/1987 | Montaldi |
| 4,718,429 A | 1/1988 | Smidt et al. |
| 4,741,338 A | 5/1988 | Miyamae et al. |
| 4,764,463 A | 8/1988 | Mason et al. |
| 4,802,475 A | 2/1989 | Weshahy et al. |
| 4,832,022 A | 5/1989 | Tjulkov et al. |
| 4,846,176 A | 7/1989 | Golden |
| 4,850,340 A | 7/1989 | Onishi |
| 4,869,250 A | 9/1989 | Bitterly |
| 4,880,564 A | 11/1989 | Abel et al. |
| 4,905,697 A | 3/1990 | Heggs et al. |
| 4,906,463 A | 3/1990 | Cleary et al. |
| 4,930,317 A | 6/1990 | Klein |
| 4,935,345 A | 6/1990 | Guibeau et al. |
| 4,961,422 A | 10/1990 | Marchosky et al. |
| 4,962,761 A | 10/1990 | Golden |
| 4,990,144 A | 2/1991 | Blott |
| 5,007,433 A | 4/1991 | Hermsdorffer et al. |
| 5,018,521 A | 5/1991 | Campbell |
| 5,024,650 A | 6/1991 | Hagiwara et al. |
| 5,065,752 A | 11/1991 | Sessions et al. |
| 5,069,208 A | 12/1991 | Noppel et al. |
| 5,084,671 A | 1/1992 | Miyata et al. |
| 5,108,390 A | 4/1992 | Potocky et al. |
| 5,119,674 A | 6/1992 | Nielsen et al. |
| 5,139,496 A | 8/1992 | Hed et al. |
| 5,143,063 A | 9/1992 | Fellner |
| 5,148,804 A | 9/1992 | Hill et al. |
| 5,158,070 A | 10/1992 | Dory |
| 5,169,384 A | 12/1992 | Bosniak et al. |
| 5,197,466 A | 3/1993 | Marchosky et al. |
| 5,207,674 A | 5/1993 | Hamilton |
| 5,221,726 A | 6/1993 | Dabi et al. |
| 5,264,234 A | 11/1993 | Windhab et al. |
| 5,277,030 A | 1/1994 | Miller |
| 5,314,423 A | 5/1994 | Seney |
| 5,327,886 A | 7/1994 | Chiu |
| 5,330,745 A | 7/1994 | McDow |
| 5,334,131 A | 8/1994 | Omandam et al. |
| 5,336,616 A | 8/1994 | Livesey et al. |
| 5,339,541 A | 8/1994 | Owens |
| 5,342,617 A | 8/1994 | Gold |
| 5,351,677 A | 10/1994 | Kami et al. |
| 5,358,467 A | 10/1994 | Milstein et al. |
| 5,362,966 A | 11/1994 | Rosenthal et al. |
| 5,372,608 A | 12/1994 | Johnson |
| 5,386,837 A | 2/1995 | Sterzer |
| 5,411,541 A | 5/1995 | Bell et al. |
| 5,427,772 A | 6/1995 | Hagan |
| 5,433,717 A | 7/1995 | Rubinsky et al. |
| 5,456,703 A | 10/1995 | Beeuwkes, III |
| 5,472,416 A | 12/1995 | Blugerman et al. |
| 5,486,207 A | 1/1996 | Mahawili |
| 5,497,596 A | 3/1996 | Zatkulak |
| 5,505,726 A | 4/1996 | Meserol |
| 5,505,730 A | 4/1996 | Edwards |
| 5,507,790 A | 4/1996 | Weiss et al. |
| 5,514,105 A | 5/1996 | Goodman, Jr. et al. |
| 5,514,170 A | 5/1996 | Mauch |
| 5,516,505 A | 5/1996 | McDow |
| 5,531,742 A | 7/1996 | Barken |
| 5,562,604 A | 10/1996 | Yablon et al. |
| 5,571,801 A | 11/1996 | Segall et al. |
| 5,575,812 A | 11/1996 | Owens et al. |
| 5,603,221 A | 2/1997 | Maytal et al. |
| 5,628,769 A | 5/1997 | Saringer et al. |
| 5,634,890 A | 6/1997 | Morris |
| 5,634,940 A | 6/1997 | Panyard |
| 5,647,051 A | 7/1997 | Neer |
| 5,647,868 A | 7/1997 | Chinn |
| 5,650,450 A | 7/1997 | Lovette et al. |
| 5,651,773 A | 7/1997 | Perry et al. |
| 5,654,279 A | 8/1997 | Rubinsky et al. |
| 5,654,546 A | 8/1997 | Lindsay |
| 5,660,836 A | 8/1997 | Knowlton |
| 5,665,053 A | 9/1997 | Jacobs |
| 5,672,172 A | 9/1997 | Zupkas |
| 5,700,284 A | 12/1997 | Owens et al. |
| 5,725,483 A | 3/1998 | Podolsky |
| 5,733,280 A | 3/1998 | Avitall |
| 5,741,248 A | 4/1998 | Stern et al. |
| 5,746,736 A | 5/1998 | Tankovich |
| 5,755,663 A | 5/1998 | Larsen et al. |
| 5,755,753 A | 5/1998 | Knowlton |
| 5,755,755 A | 5/1998 | Panyard |
| 5,759,182 A | 6/1998 | Varney et al. |
| 5,759,764 A | 6/1998 | Polovina |
| 5,769,879 A | 6/1998 | Richards et al. |
| 5,785,955 A | 7/1998 | Fischer |
| 5,792,080 A | 8/1998 | Ookawa et al. |
| 5,814,040 A | 9/1998 | Nelson et al. |
| 5,817,050 A | 10/1998 | Klein |
| 5,817,149 A | 10/1998 | Owens et al. |
| 5,817,150 A | 10/1998 | Owens et al. |
| 5,830,208 A | 11/1998 | Muller |
| 5,833,685 A | 11/1998 | Tortal et al. |
| 5,844,013 A | 12/1998 | Kenndoff et al. |
| 5,871,524 A | 2/1999 | Knowlton |
| 5,871,526 A | 2/1999 | Gibbs et al. |
| 5,885,211 A | 3/1999 | Eppstein et al. |
| 5,895,418 A | 4/1999 | Saringer et al. |
| 5,901,707 A | 5/1999 | Goncalves et al. |

(56) References Cited

U.S. PATENT DOCUMENTS

| | | |
|---|---|---|
| 5,902,256 A | 5/1999 | Benaron |
| 5,919,219 A | 7/1999 | Knowlton |
| 5,944,748 A | 8/1999 | Mager et al. |
| 5,948,011 A | 9/1999 | Knowlton |
| 5,954,680 A | 9/1999 | Augustine et al. |
| 5,964,092 A | 10/1999 | Tozuka et al. |
| 5,964,749 A | 10/1999 | Eckhouse et al. |
| 5,967,976 A | 10/1999 | Larsen et al. |
| 5,986,167 A | 11/1999 | Arteman et al. |
| 5,989,286 A | 11/1999 | Owens et al. |
| 5,997,530 A | 12/1999 | Nelson et al. |
| 6,017,337 A | 1/2000 | Pira et al. |
| 6,023,932 A | 2/2000 | Johnston et al. |
| 6,032,675 A | 3/2000 | Rubinsky |
| 6,039,694 A | 3/2000 | Larson et al. |
| 6,041,787 A | 3/2000 | Rubinsky |
| 6,049,927 A | 4/2000 | Thomas et al. |
| 6,051,159 A | 4/2000 | Hao et al. |
| 6,074,415 A | 6/2000 | Der Ovanesian |
| 6,093,230 A | 7/2000 | Johnson, III et al. |
| 6,102,885 A | 8/2000 | Bass |
| 6,104,952 A | 8/2000 | Tu et al. |
| 6,104,959 A | 8/2000 | Spertell et al. |
| 6,106,517 A | 8/2000 | Zupkas |
| 6,113,558 A | 9/2000 | Rosenschein et al. |
| 6,113,559 A | 9/2000 | Klopotek |
| 6,113,626 A | 9/2000 | Clifton et al. |
| 6,120,519 A | 9/2000 | Weber et al. |
| 6,151,735 A | 11/2000 | Koby et al. |
| 6,152,952 A | 11/2000 | Owens et al. |
| 6,171,301 B1 | 1/2001 | Nelson et al. |
| 6,226,996 B1 | 5/2001 | Weber et al. |
| 6,241,753 B1 | 6/2001 | Knowlton |
| 6,264,649 B1 | 7/2001 | Whitcroft et al. |
| 6,273,884 B1 | 8/2001 | Altshuler et al. |
| 6,290,988 B1 | 9/2001 | Van Vilsteren et al. |
| 6,311,090 B1 | 10/2001 | Knowlton |
| 6,311,497 B1 | 11/2001 | Chung et al. |
| 6,312,453 B1 | 11/2001 | Stefanile et al. |
| 6,350,276 B1 | 2/2002 | Knowlton |
| 6,354,297 B1 | 3/2002 | Eiseman |
| 6,357,907 B1 | 3/2002 | Cleveland et al. |
| 6,375,673 B1 | 4/2002 | Clifton et al. |
| 6,377,854 B1 | 4/2002 | Knowlton |
| 6,377,855 B1 | 4/2002 | Knowlton |
| 6,381,497 B1 | 4/2002 | Knowlton |
| 6,381,498 B1 | 4/2002 | Knowlton |
| 6,387,380 B1 | 5/2002 | Knowlton |
| 6,401,722 B1 | 6/2002 | Krad |
| 6,405,090 B1 | 6/2002 | Knowlton |
| 6,413,255 B1 | 7/2002 | Stern |
| 6,425,912 B1 | 7/2002 | Knowlton |
| 6,426,445 B1 | 7/2002 | Young et al. |
| 6,430,446 B1 | 8/2002 | Knowlton |
| 6,430,956 B1 | 8/2002 | Haas et al. |
| 6,438,424 B1 | 8/2002 | Knowlton |
| 6,438,964 B1 | 8/2002 | Giblin |
| 6,453,202 B1 | 9/2002 | Knowlton |
| 6,458,888 B1 | 10/2002 | Hood et al. |
| 6,461,378 B1 | 10/2002 | Knowlton |
| 6,470,216 B1 | 10/2002 | Knowlton |
| 6,471,693 B1 | 10/2002 | Carroll et al. |
| 6,475,211 B2 | 11/2002 | Chess et al. |
| 6,494,844 B1 | 12/2002 | Van Bladel et al. |
| 6,497,721 B2 | 12/2002 | Ginsburg et al. |
| 6,508,831 B1 | 1/2003 | Kushnir |
| 6,514,244 B2 | 2/2003 | Pope et al. |
| 6,519,964 B2 | 2/2003 | Bieberich |
| 6,523,354 B1 | 2/2003 | Tolbert |
| 6,527,765 B2 | 3/2003 | Kelman et al. |
| 6,527,798 B2 | 3/2003 | Ginsburg et al. |
| 6,544,248 B1 | 4/2003 | Bass |
| 6,548,297 B1 | 4/2003 | Kuri-Harcuch et al. |
| 6,551,348 B1 | 4/2003 | Blalock et al. |
| 6,551,349 B2 | 4/2003 | Lasheras et al. |
| 6,569,189 B1 | 5/2003 | Augustine et al. |
| 6,585,652 B2 | 7/2003 | Lang et al. |
| 6,592,577 B2 | 7/2003 | Abboud et al. |
| 6,605,080 B1 | 8/2003 | Altshuler et al. |
| 6,620,188 B1 | 9/2003 | Ginsburg et al. |
| 6,620,189 B1 | 9/2003 | Machold et al. |
| 6,623,430 B1 | 9/2003 | Slayton et al. |
| 6,626,854 B2 | 9/2003 | Friedman et al. |
| 6,632,219 B1 | 10/2003 | Baranov et al. |
| 6,635,053 B1 | 10/2003 | Lalonde et al. |
| 6,645,162 B2 | 11/2003 | Friedman et al. |
| 6,645,229 B2 | 11/2003 | Matsumura et al. |
| 6,648,904 B2 | 11/2003 | Altshuler et al. |
| 6,656,208 B2 | 12/2003 | Grahn et al. |
| 6,662,054 B2 | 12/2003 | Kreindel et al. |
| 6,682,550 B2 | 1/2004 | Clifton et al. |
| 6,685,731 B2 | 2/2004 | Kushnir et al. |
| 6,695,874 B2 | 2/2004 | Machold et al. |
| 6,699,266 B2 | 3/2004 | Lachenbruch et al. |
| 6,718,785 B2 | 4/2004 | Bieberich |
| 6,741,895 B1 | 5/2004 | Gafni et al. |
| 6,743,222 B2 | 6/2004 | Durkin et al. |
| 6,746,474 B2 | 6/2004 | Saadat |
| 6,749,624 B2 | 6/2004 | Knowlton |
| 6,764,493 B1 | 7/2004 | Weber et al. |
| 6,764,502 B2 | 7/2004 | Bieberich |
| 6,789,545 B2 | 9/2004 | Littrup et al. |
| 6,820,961 B2 | 11/2004 | Johnson |
| 6,821,274 B2 | 11/2004 | McHale et al. |
| 6,840,955 B2 | 1/2005 | Ein |
| 6,849,075 B2 | 2/2005 | Bertolero et al. |
| 6,878,144 B2 | 4/2005 | Altshuler et al. |
| 6,889,090 B2 | 5/2005 | Kreindel |
| 6,904,956 B2 | 6/2005 | Noel |
| 6,918,903 B2 | 7/2005 | Bass |
| 6,927,316 B1 | 8/2005 | Faries, Jr. et al. |
| 6,942,022 B2 | 9/2005 | Blangetti et al. |
| 6,945,942 B2 | 9/2005 | Van Bladel et al. |
| 6,948,903 B2 | 9/2005 | Ablabutyan et al. |
| 7,005,558 B1 | 2/2006 | Johansson et al. |
| 7,022,121 B2 | 4/2006 | Stern et al. |
| 7,037,326 B2 | 5/2006 | Lee et al. |
| 7,060,061 B2 | 6/2006 | Altshuler et al. |
| 7,077,858 B2 | 7/2006 | Fletcher et al. |
| 7,081,111 B2 | 7/2006 | Svaasand et al. |
| 7,096,204 B1 | 8/2006 | Chen et al. |
| 7,112,712 B1 | 9/2006 | Ancell |
| 7,115,123 B2 | 10/2006 | Knowlton et al. |
| 7,183,360 B2 | 2/2007 | Daniel et al. |
| 7,189,252 B2 | 3/2007 | Krueger |
| 7,192,426 B2 | 3/2007 | Baust et al. |
| 7,204,832 B2 | 4/2007 | Altshuler et al. |
| 7,220,778 B2 | 5/2007 | Anderson et al. |
| 7,258,674 B2 | 8/2007 | Cribbs et al. |
| 7,276,058 B2 | 10/2007 | Altshuler et al. |
| 7,367,341 B2 | 5/2008 | Anderson et al. |
| 7,572,268 B2 | 8/2009 | Babaev |
| 7,604,632 B2 | 10/2009 | Howlett et al. |
| 7,613,523 B2 | 11/2009 | Eggers et al. |
| 7,615,016 B2 | 11/2009 | Barthe et al. |
| 7,713,266 B2 | 5/2010 | Elkins et al. |
| 7,780,656 B2 | 8/2010 | Tankovich |
| 7,799,018 B2 | 9/2010 | Goulko |
| 7,824,437 B1 | 11/2010 | Saunders |
| 7,850,683 B2 | 12/2010 | Elkins et al. |
| 7,854,754 B2 | 12/2010 | Ting et al. |
| 7,862,558 B2 | 1/2011 | Elkins et al. |
| 7,959,657 B1 | 6/2011 | Harsy et al. |
| 7,963,959 B2 | 6/2011 | Da Silva et al. |
| 7,993,330 B2 | 8/2011 | Goulko |
| 7,998,137 B2 | 8/2011 | Elkins et al. |
| 8,133,180 B2 | 3/2012 | Slayton et al. |
| 8,246,611 B2 | 8/2012 | Paithankar et al. |
| 8,333,700 B1 | 12/2012 | Barthe et al. |
| 8,366,622 B2 | 2/2013 | Slayton et al. |
| 8,372,130 B2 | 2/2013 | Young et al. |
| 8,397,518 B1 | 3/2013 | Vistakula et al. |
| 8,414,631 B2 | 4/2013 | Quisenberry et al. |
| 8,433,400 B2 | 4/2013 | Prushinskaya et al. |

(56) References Cited

U.S. PATENT DOCUMENTS

| | | |
|---|---|---|
| 8,506,486 B2 | 8/2013 | Slayton et al. |
| 8,523,775 B2 | 9/2013 | Barthe et al. |
| 8,523,791 B2 | 9/2013 | Castel |
| 8,523,927 B2 | 9/2013 | Levinson et al. |
| 8,535,228 B2 | 9/2013 | Slayton et al. |
| 8,603,073 B2 | 12/2013 | Allison |
| 8,636,665 B2 | 1/2014 | Slayton et al. |
| 8,641,622 B2 | 2/2014 | Barthe et al. |
| 8,663,112 B2 | 3/2014 | Slayton et al. |
| 8,672,848 B2 | 3/2014 | Slayton et al. |
| 8,676,332 B2 | 3/2014 | Fahey |
| 8,690,778 B2 | 4/2014 | Slayton et al. |
| 8,690,779 B2 | 4/2014 | Slayton et al. |
| 8,690,780 B2 | 4/2014 | Slayton et al. |
| 8,702,774 B2 | 4/2014 | Baker et al. |
| 8,758,215 B2 | 6/2014 | Legendre et al. |
| 8,764,693 B1 | 7/2014 | Graham et al. |
| 8,834,547 B2 | 9/2014 | Anderson et al. |
| 2001/0005791 A1 | 6/2001 | Ginsburg et al. |
| 2001/0007952 A1 | 7/2001 | Shimizu |
| 2001/0023364 A1 | 9/2001 | Ahn |
| 2001/0031459 A1 | 10/2001 | Fahy et al. |
| 2001/0039439 A1 | 11/2001 | Elkins et al. |
| 2001/0045104 A1 | 11/2001 | Bailey et al. |
| 2001/0047196 A1 | 11/2001 | Ginsburg et al. |
| 2002/0026226 A1 | 2/2002 | Ein |
| 2002/0032473 A1 | 3/2002 | Kushnir et al. |
| 2002/0042607 A1 | 4/2002 | Palmer et al. |
| 2002/0049483 A1 | 4/2002 | Knowlton |
| 2002/0058975 A1 | 5/2002 | Bieberich |
| 2002/0062142 A1 | 5/2002 | Knowlton |
| 2002/0082668 A1 | 6/2002 | Ingman |
| 2002/0103520 A1 | 8/2002 | Latham |
| 2002/0107558 A1 | 8/2002 | Clifton et al. |
| 2002/0117293 A1 | 8/2002 | Campbell |
| 2002/0151830 A1 | 10/2002 | Kahn |
| 2002/0151887 A1 | 10/2002 | Stern et al. |
| 2002/0156509 A1 | 10/2002 | Cheung |
| 2002/0188286 A1 | 12/2002 | Quijano et al. |
| 2003/0032900 A1 | 2/2003 | Ella |
| 2003/0044764 A1 | 3/2003 | Soane et al. |
| 2003/0055414 A1 | 3/2003 | Altshuler et al. |
| 2003/0062040 A1 | 4/2003 | Lurie et al. |
| 2003/0069618 A1 | 4/2003 | Smith et al. |
| 2003/0077329 A1 | 4/2003 | Kipp et al. |
| 2003/0079488 A1 | 5/2003 | Bieberich |
| 2003/0100936 A1 | 5/2003 | Altshuler et al. |
| 2003/0109908 A1 | 6/2003 | Lachenbruch et al. |
| 2003/0109910 A1 | 6/2003 | Lachenbruch et al. |
| 2003/0109911 A1 | 6/2003 | Lachenbruch et al. |
| 2003/0114885 A1 | 6/2003 | Nova et al. |
| 2003/0120268 A1 | 6/2003 | Bertolero et al. |
| 2003/0125649 A1 | 7/2003 | McIntosh et al. |
| 2003/0187488 A1 | 10/2003 | Kreindel et al. |
| 2003/0199226 A1 | 10/2003 | Sommer et al. |
| 2003/0199859 A1 | 10/2003 | Altshuler et al. |
| 2003/0220594 A1 | 11/2003 | Halvorson et al. |
| 2003/0220674 A1 | 11/2003 | Anderson et al. |
| 2003/0236487 A1 | 12/2003 | Knowlton |
| 2004/0006328 A1 | 1/2004 | Anderson |
| 2004/0009936 A1 | 1/2004 | Tang et al. |
| 2004/0024437 A1 | 2/2004 | Machold et al. |
| 2004/0030332 A1 | 2/2004 | Knowlton et al. |
| 2004/0034341 A1 | 2/2004 | Altshuler et al. |
| 2004/0039312 A1 | 2/2004 | Hillstead et al. |
| 2004/0044384 A1 | 3/2004 | Leber et al. |
| 2004/0049178 A1 | 3/2004 | Abboud et al. |
| 2004/0073079 A1 | 4/2004 | Altshuler et al. |
| 2004/0074629 A1 | 4/2004 | Noel |
| 2004/0077977 A1 | 4/2004 | Ella et al. |
| 2004/0082886 A1 | 4/2004 | Timpson |
| 2004/0093042 A1 | 5/2004 | Altshuler et al. |
| 2004/0104012 A1 | 6/2004 | Zhou et al. |
| 2004/0106867 A1 | 6/2004 | Eshel et al. |
| 2004/0133251 A1 | 7/2004 | Altshuler et al. |
| 2004/0162596 A1 | 8/2004 | Altshuler et al. |
| 2004/0199226 A1 | 10/2004 | Shadduck |
| 2004/0210214 A1 | 10/2004 | Knowlton |
| 2004/0210287 A1 | 10/2004 | Greene |
| 2004/0249427 A1 | 12/2004 | Nabilsi et al. |
| 2004/0259855 A1 | 12/2004 | Anderson et al. |
| 2004/0260209 A1 | 12/2004 | Ella et al. |
| 2004/0260210 A1 | 12/2004 | Ella et al. |
| 2004/0260211 A1 | 12/2004 | Maalouf |
| 2005/0010197 A1 | 1/2005 | Lau et al. |
| 2005/0049526 A1 | 3/2005 | Baer |
| 2005/0049543 A1 | 3/2005 | Anderson et al. |
| 2005/0049661 A1 | 3/2005 | Koffroth |
| 2005/0113725 A1 | 5/2005 | Masuda |
| 2005/0145372 A1 | 7/2005 | Noel |
| 2005/0154431 A1 | 7/2005 | Quistgaard et al. |
| 2005/0159986 A1 | 7/2005 | Breeland et al. |
| 2005/0177075 A1 | 8/2005 | Meunier et al. |
| 2005/0182462 A1 | 8/2005 | Chornenky et al. |
| 2005/0187597 A1 | 8/2005 | Vanderschuit |
| 2005/0203446 A1 | 9/2005 | Takashima |
| 2005/0215987 A1 | 9/2005 | Slatkine |
| 2005/0222565 A1 | 10/2005 | Manstein |
| 2005/0251117 A1 | 11/2005 | Anderson et al. |
| 2005/0251120 A1 | 11/2005 | Anderson et al. |
| 2005/0277859 A1 | 12/2005 | Carlsmith et al. |
| 2005/0283144 A1 | 12/2005 | Shiono et al. |
| 2006/0030778 A1 | 2/2006 | Mendlein et al. |
| 2006/0036300 A1 | 2/2006 | Kreindel |
| 2006/0074313 A1 | 4/2006 | Slayton et al. |
| 2006/0079852 A1 | 4/2006 | Bubb et al. |
| 2006/0122509 A1 | 6/2006 | Desilets |
| 2006/0189964 A1 | 8/2006 | Anderson et al. |
| 2006/0195168 A1 | 8/2006 | Dunbar et al. |
| 2006/0200063 A1 | 9/2006 | Munro et al. |
| 2006/0206040 A1 | 9/2006 | Greenberg et al. |
| 2006/0234899 A1 | 10/2006 | Nekmard et al. |
| 2006/0259102 A1 | 11/2006 | Slatkine |
| 2006/0270745 A1 | 11/2006 | Hunt et al. |
| 2006/0293734 A1 | 12/2006 | Scott et al. |
| 2007/0010861 A1 | 1/2007 | Anderson et al. |
| 2007/0032561 A1 | 2/2007 | Lin et al. |
| 2007/0038156 A1 | 2/2007 | Rosenberg |
| 2007/0073367 A1 | 3/2007 | Jones et al. |
| 2007/0088413 A1* | 4/2007 | Weber .................... A61B 18/14 607/99 |
| 2007/0129714 A1 | 6/2007 | Elkins et al. |
| 2007/0135876 A1 | 6/2007 | Weber |
| 2007/0141265 A1 | 6/2007 | Thomson |
| 2007/0179482 A1 | 8/2007 | Anderson et al. |
| 2007/0198071 A1 | 8/2007 | Ting et al. |
| 2007/0239075 A1 | 10/2007 | Rosenberg et al. |
| 2007/0249519 A1 | 10/2007 | Guha et al. |
| 2007/0255187 A1 | 11/2007 | Branch |
| 2007/0255362 A1* | 11/2007 | Levinson ................. A61F 7/10 607/96 |
| 2007/0265585 A1 | 11/2007 | Joshi et al. |
| 2007/0270925 A1 | 11/2007 | Levinson |
| 2007/0282249 A1 | 12/2007 | Quisenberry et al. |
| 2008/0046047 A1 | 2/2008 | Jacobs |
| 2008/0058784 A1 | 3/2008 | Manstein et al. |
| 2008/0077201 A1 | 3/2008 | Levinson et al. |
| 2008/0077202 A1 | 3/2008 | Levinson |
| 2008/0077211 A1* | 3/2008 | Levinson et al. ............. 607/108 |
| 2008/0097207 A1 | 4/2008 | Cai et al. |
| 2008/0139901 A1 | 6/2008 | Altshuler et al. |
| 2008/0140061 A1 | 6/2008 | Toubia et al. |
| 2008/0140371 A1 | 6/2008 | Warner |
| 2008/0161892 A1 | 7/2008 | Mercuro et al. |
| 2008/0183164 A1 | 7/2008 | Elkins et al. |
| 2008/0188915 A1* | 8/2008 | Mills ....................... A61F 7/007 607/112 |
| 2008/0269851 A1 | 10/2008 | Deem et al. |
| 2008/0287839 A1 | 11/2008 | Rosen et al. |
| 2009/0012434 A1 | 1/2009 | Anderson |
| 2009/0018623 A1 | 1/2009 | Levinson et al. |
| 2009/0018624 A1 | 1/2009 | Levinson et al. |
| 2009/0018625 A1 | 1/2009 | Levinson et al. |
| 2009/0018626 A1 | 1/2009 | Levinson et al. |

(56) References Cited

U.S. PATENT DOCUMENTS

| | | | |
|---|---|---|---|
| 2009/0018627 A1 | 1/2009 | Levinson et al. |
| 2009/0112134 A1 | 4/2009 | Avni |
| 2009/0118722 A1* | 5/2009 | Ebbers | A61B 18/02 606/21 |
| 2009/0149929 A1 | 6/2009 | Levinson et al. |
| 2009/0149930 A1 | 6/2009 | Schenck |
| 2009/0171334 A1 | 7/2009 | Elkins et al. |
| 2009/0276018 A1 | 11/2009 | Brader |
| 2009/0299234 A1 | 12/2009 | Cho et al. |
| 2009/0312676 A1 | 12/2009 | Rousso et al. |
| 2009/0312693 A1 | 12/2009 | Thapliyal et al. |
| 2010/0015190 A1 | 1/2010 | Hassler |
| 2010/0030306 A1 | 2/2010 | Edelman et al. |
| 2010/0036295 A1 | 2/2010 | Altshuler et al. |
| 2010/0042087 A1 | 2/2010 | Goldboss et al. |
| 2010/0049178 A1 | 2/2010 | Deem et al. |
| 2010/0081971 A1 | 4/2010 | Allison |
| 2010/0087806 A1 | 4/2010 | Da Silva et al. |
| 2010/0152824 A1 | 6/2010 | Allison |
| 2010/0168726 A1 | 7/2010 | Brookman |
| 2010/0179531 A1* | 7/2010 | Nebrigic | A61B 18/14 606/33 |
| 2010/0198064 A1 | 8/2010 | Perl et al. |
| 2010/0217349 A1 | 8/2010 | Fahey et al. |
| 2010/0268220 A1 | 10/2010 | Johnson et al. |
| 2010/0280582 A1 | 11/2010 | Baker et al. |
| 2011/0040235 A1 | 2/2011 | Castel |
| 2011/0040299 A1 | 2/2011 | Kim et al. |
| 2011/0046523 A1 | 2/2011 | Altshuler et al. |
| 2011/0060323 A1 | 3/2011 | Baust et al. |
| 2011/0066083 A1 | 3/2011 | Tosaya et al. |
| 2011/0077557 A1 | 3/2011 | Wing et al. |
| 2011/0077723 A1 | 3/2011 | Parish et al. |
| 2011/0112520 A1 | 5/2011 | Kreindel |
| 2011/0144631 A1 | 6/2011 | Elkins et al. |
| 2011/0152849 A1 | 6/2011 | Baust et al. |
| 2011/0172651 A1 | 7/2011 | Altshuler et al. |
| 2011/0189129 A1 | 8/2011 | Qiu et al. |
| 2011/0196395 A1 | 8/2011 | Maschke |
| 2011/0202048 A1* | 8/2011 | Nebrigic | A61F 7/007 606/22 |
| 2011/0257642 A1 | 10/2011 | Griggs, III |
| 2011/0301585 A1 | 12/2011 | Goulko |
| 2011/0313411 A1 | 12/2011 | Anderson et al. |
| 2011/0313412 A1 | 12/2011 | Kim et al. |
| 2012/0010609 A1 | 1/2012 | Deem et al. |
| 2012/0022518 A1 | 1/2012 | Levinson |
| 2012/0022622 A1 | 1/2012 | Johnson et al. |
| 2012/0065629 A1 | 3/2012 | Elkins et al. |
| 2012/0083862 A1 | 4/2012 | Altshuler et al. |
| 2012/0109041 A1 | 5/2012 | Munz |
| 2012/0158100 A1 | 6/2012 | Schomacker |
| 2012/0209363 A1 | 8/2012 | Williams, III et al. |
| 2012/0233736 A1 | 9/2012 | Tepper et al. |
| 2012/0253416 A1 | 10/2012 | Erez et al. |
| 2012/0259322 A1 | 10/2012 | Fourkas et al. |
| 2012/0277674 A1 | 11/2012 | Clark, III et al. |
| 2012/0310232 A1 | 12/2012 | Erez |
| 2013/0018236 A1 | 1/2013 | Altshuler et al. |
| 2013/0019374 A1 | 1/2013 | Schwartz |
| 2013/0073017 A1 | 3/2013 | Liu et al. |
| 2013/0079684 A1 | 3/2013 | Rosen et al. |
| 2013/0150844 A1 | 6/2013 | Deem et al. |
| 2013/0166003 A1 | 6/2013 | Johnson et al. |
| 2013/0190744 A1 | 7/2013 | Avram et al. |
| 2013/0238062 A1 | 9/2013 | Ron Edoute et al. |
| 2013/0245507 A1 | 9/2013 | Khorassani Zadeh |
| 2013/0253384 A1 | 9/2013 | Anderson et al. |
| 2013/0253493 A1 | 9/2013 | Anderson et al. |
| 2013/0253494 A1 | 9/2013 | Anderson et al. |
| 2013/0253495 A1 | 9/2013 | Anderson et al. |
| 2013/0253496 A1 | 9/2013 | Anderson et al. |
| 2013/0331914 A1 | 12/2013 | Lee et al. |
| 2014/0005759 A1 | 1/2014 | Fahey et al. |
| 2014/0005760 A1 | 1/2014 | Levinson et al. |
| 2014/0067025 A1 | 3/2014 | Levinson et al. |
| 2014/0142469 A1 | 5/2014 | Britva et al. |
| 2014/0200487 A1 | 7/2014 | Ramdas et al. |
| 2014/0200488 A1 | 7/2014 | Seo et al. |
| 2014/0222121 A1 | 8/2014 | Spence et al. |
| 2014/0277219 A1 | 9/2014 | Nanda |
| 2014/0277302 A1 | 9/2014 | Weber et al. |
| 2014/0277303 A1 | 9/2014 | Biser et al. |
| 2014/0303697 A1 | 10/2014 | Anderson et al. |
| 2015/0209174 A1 | 7/2015 | Abreu |
| 2015/0216719 A1 | 8/2015 | DeBenedictis et al. |
| 2015/0216720 A1 | 8/2015 | DeBenedictis et al. |
| 2015/0216816 A1 | 8/2015 | O'Neil et al. |
| 2015/0223975 A1 | 8/2015 | Anderson et al. |
| 2015/0328077 A1 | 11/2015 | Levinson |
| 2015/0335468 A1 | 11/2015 | Rose et al. |
| 2015/0342780 A1 | 12/2015 | Levinson et al. |
| 2016/0051308 A1 | 2/2016 | Pennybacker et al. |
| 2016/0051401 A1 | 2/2016 | Yee et al. |
| 2016/0135985 A1 | 5/2016 | Anderson |
| 2016/0324684 A1 | 11/2016 | Levinson et al. |
| 2017/0079833 A1 | 3/2017 | Frangineas, Jr. et al. |
| 2017/0105869 A1 | 4/2017 | Frangineas, Jr. et al. |
| 2017/0165105 A1 | 6/2017 | Anderson et al. |
| 2017/0196731 A1 | 7/2017 | Debenedictis et al. |
| 2017/0239079 A1 | 8/2017 | Root et al. |
| 2017/0325992 A1 | 11/2017 | DeBenedictis et al. |
| 2017/0325993 A1 | 11/2017 | Jimenez Lozano et al. |
| 2017/0326042 A1 | 11/2017 | Zeng et al. |
| 2017/0326346 A1 | 11/2017 | Jimenez Lozano et al. |

FOREIGN PATENT DOCUMENTS

| | | |
|---|---|---|
| CH | 333982 A | 11/1958 |
| CN | 86200604 U | 10/1987 |
| CN | 2514795 Y | 10/2002 |
| CN | 1511503 A | 7/2004 |
| CN | 1741777 A | 3/2006 |
| CN | 1817990 A | 8/2006 |
| CN | 2843367 Y | 12/2006 |
| CN | 2850584 Y | 12/2006 |
| CN | 2850585 Y | 12/2006 |
| CN | 200970265 Y | 11/2007 |
| DE | 532976 C | 9/1931 |
| DE | 2851602 | 6/1980 |
| DE | 4213584 A1 | 11/1992 |
| DE | 4224595 | 1/1994 |
| DE | 4238291 | 5/1994 |
| DE | 4445627 A1 | 6/1996 |
| DE | 19800416 A1 | 7/1999 |
| EP | 0263069 A2 | 4/1988 |
| EP | 0397043 | 11/1990 |
| EP | 0406244 A1 | 1/1991 |
| EP | 0598824 A1 | 6/1994 |
| EP | 1030611 A1 | 8/2000 |
| EP | 1568395 A1 | 8/2005 |
| EP | 2260801 A2 | 12/2010 |
| EP | 2289598 A1 | 3/2011 |
| EP | 2527005 A1 | 11/2012 |
| FR | 854937 A | 4/1940 |
| FR | 2744358 A1 | 8/1997 |
| FR | 2767476 A1 | 2/1999 |
| FR | 2776920 A1 | 10/1999 |
| FR | 2789893 A1 | 8/2000 |
| FR | 2805989 A1 | 9/2001 |
| GB | 387960 A | 2/1933 |
| GB | 2120944 A | 12/1983 |
| GB | 2248183 A | 4/1992 |
| GB | 2263872 A | 8/1993 |
| GB | 2286660 A | 8/1995 |
| GB | 2323659 A | 9/1998 |
| JP | 63076895 A | 4/1988 |
| JP | 01223961 A | 9/1989 |
| JP | 10223961 | 9/1989 |
| JP | 03051964 A | 3/1991 |
| JP | 3259975 A | 11/1991 |
| JP | 4093597 A | 3/1992 |
| JP | 6282977 A | 10/1994 |
| JP | 7194666 | 8/1995 |

(56) References Cited

FOREIGN PATENT DOCUMENTS

| | | |
|---|---|---|
| JP | 7268274 A | 10/1995 |
| JP | 09164163 A | 6/1997 |
| JP | 10216169 A | 8/1998 |
| JP | 3065657 | 11/1999 |
| JP | 2000503154 A | 3/2000 |
| JP | 2001046416 A | 2/2001 |
| JP | 2002543668 A | 12/2002 |
| JP | 2004013600 A | 1/2004 |
| JP | 2004159666 A | 6/2004 |
| JP | 2004073812 | 11/2004 |
| JP | 2005039790 A | 2/2005 |
| JP | 3655820 | 3/2005 |
| JP | 200565984 | 3/2005 |
| JP | 2005110755 | 4/2005 |
| JP | 2005520608 | 7/2005 |
| JP | 2005237908 A | 9/2005 |
| JP | 2008323716 | 11/2005 |
| JP | 2006026001 A | 2/2006 |
| JP | 2006130055 | 5/2006 |
| JP | 2005520608 | 7/2006 |
| JP | 2006520949 A | 9/2006 |
| JP | 2008532591 | 8/2008 |
| JP | 2009189757 A | 8/2009 |
| KR | 200173222 Y1 | 12/1999 |
| KR | 102004009450 | 11/2004 |
| KR | 20090000258 U | 1/2009 |
| KR | 1020130043299 A | 4/2013 |
| KR | 1020140038165 A | 3/2014 |
| RU | 2036667 01 | 6/1995 |
| SU | 532976 | 11/1978 |
| TW | 0476644 | 2/2002 |
| WO | WO1985003216 | 8/1985 |
| WO | WO97/05828 | 11/1990 |
| WO | 9114417 A1 | 10/1991 |
| WO | WO94/04116 | 3/1994 |
| WO | 9623447 A1 | 8/1996 |
| WO | 9626693 A1 | 9/1996 |
| WO | WO-96/36293 | 11/1996 |
| WO | WO-96/37158 | 11/1996 |
| WO | WO96/37158 | 11/1996 |
| WO | WO9636293 | 11/1996 |
| WO | 9704832 A1 | 2/1997 |
| WO | WO97/05828 | 2/1997 |
| WO | WO-97/05828 | 2/1997 |
| WO | WO9722262 | 6/1997 |
| WO | WO-9722262 A2 | 6/1997 |
| WO | 9724088 A1 | 7/1997 |
| WO | 9748440 A1 | 12/1997 |
| WO | 9829134 A2 | 7/1998 |
| WO | 9831321 A1 | 7/1998 |
| WO | WO-98/41157 | 9/1998 |
| WO | WO-9841156 A1 | 9/1998 |
| WO | WO9841157 | 9/1998 |
| WO | 9909928 A1 | 3/1999 |
| WO | 9916502 A1 | 4/1999 |
| WO | WO9938469 | 8/1999 |
| WO | WO-9938469 A1 | 8/1999 |
| WO | 9949937 A1 | 10/1999 |
| WO | WO-00/44346 | 8/2000 |
| WO | WO2000067685 | 11/2000 |
| WO | 0100269 A1 | 1/2001 |
| WO | 0113989 A1 | 3/2001 |
| WO | WO0114012 | 3/2001 |
| WO | WO2001014012 | 3/2001 |
| WO | 0134048 A1 | 5/2001 |
| WO | WO-0205736 A2 | 1/2002 |
| WO | WO-02/102921 | 12/2002 |
| WO | WO-200307859 A1 | 1/2003 |
| WO | WO-03078596 A2 | 9/2003 |
| WO | 03079916 A1 | 10/2003 |
| WO | WO-04/000098 | 12/2003 |
| WO | WO-04080279 A2 | 9/2004 |
| WO | WO-05046540 A1 | 5/2005 |
| WO | 2005060354 A2 | 7/2005 |
| WO | WO2005/096979 | 10/2005 |
| WO | 2005112815 A1 | 12/2005 |
| WO | WO-06066226 | 6/2006 |
| WO | WO2006094348 | 9/2006 |
| WO | 2006116603 A2 | 11/2006 |
| WO | WO-06127467 | 11/2006 |
| WO | 2007028975 A1 | 3/2007 |
| WO | WO-07041642 A2 | 4/2007 |
| WO | WO2007/127924 | 11/2007 |
| WO | 2007145421 A1 | 12/2007 |
| WO | 2007145422 A1 | 12/2007 |
| WO | 2008006018 A2 | 1/2008 |
| WO | 2008039556 A1 | 4/2008 |
| WO | WO2008039557 | 4/2008 |
| WO | 2008055243 A2 | 5/2008 |
| WO | WO2008/143678 | 11/2008 |
| WO | WO-2010077841 A1 | 7/2010 |
| WO | WO-2010127315 A2 | 11/2010 |
| WO | WO-2012012296 A1 | 1/2012 |
| WO | 2013013059 A1 | 1/2013 |
| WO | 2013075006 A1 | 5/2013 |
| WO | 2013075016 A1 | 5/2013 |
| WO | 2013190337 A1 | 12/2013 |
| WO | 2014151872 A3 | 9/2014 |
| WO | 2014191263 A1 | 12/2014 |
| WO | 2015117001 A1 | 8/2015 |
| WO | 2015117005 A1 | 8/2015 |
| WO | 2015117026 A2 | 8/2015 |
| WO | 2015117032 A1 | 8/2015 |
| WO | 2015117036 A2 | 8/2015 |
| WO | 2016028796 A1 | 2/2016 |
| WO | 2016048721 A1 | 3/2016 |

OTHER PUBLICATIONS

European Search Report, Supplement, European Patent Application No. EP08798416.7, Applicant: Zeltiq Aesthetics, Inc., dated Jan. 12, 2012, 7 pages.

European Search Report, Supplement, European Patent Application No. EP09836823, Applicant: Zeltiq Aesthetics, Inc., dated May 15, 2012, 5 pages.

Final Office Action; U.S. Appl. No. 11/741,271; dated Jul. 19, 2012, 8 pages.

Final Office Action; U.S. Appl. No. 11/750,953; dated Jul. 5, 2012, 11 pages.

International Search Report and Written Opinion for PCT/US2012/022585; dated May 18, 2012, 12 pages.

Non-Final Office Action; U.S. Appl. No. 11/528,189; dated Apr. 6, 2012, 9 pages.

Non-Final Office Action; U.S. Appl. No. 11/777,992; dated Jun. 22, 2012, 5 pages.

Pre-Interview Office Action; U.S. Appl. No. 11/434,478; dated May 6, 2010, 4 pages.

Ardevol, "Cooling rates of tissue samples during freezing with liquid nitrogen," J. of Biochem and Biophysical Methods, 27, 77-86 (1993).

Bohm et al., "Saline-enhanced radiofrequency ablation of breast tissue: an in vitro feasibility study," Invest Radiol, 2000, pp. 149-57, vol. 35—issue (3).

Bondei, E. et al., "Disorders of Subcutaneous Tissue (Cold Panniculitis)," Dermatology in General Medicine, Chapter 108, Section 16: 1333-1334, 1993.

Burge, S.M. et al., "Hair Follicle Destruction and Regeneration in Guinea Pig Skin after Cutaneous Freeze Injury," Cryobiology, 27(2): 153-163, 1990.

Coban, "Ischemia-Reperfusion Injury of Adipofascial Tissue: An Experimental Study Evaluating early Histologic and Biochemical Alterations in Rats," Mediators of Inflammation, 2005, 5, 304-308.

Disclosure re: "Method and Apparatus for Regional Fat Reduction Using Controlled and Sustained Cooling of Skin Surface".

Donski et al., "The Effects of Cooling no Experimental Free Flap Survival," Brit J Plas Surg, 1980, pp. 353-360, vol. 33.

Duncan, W.C. et al., "Cold Panniculitis," Arch. Derm., 94:722-24, 1966.

Epstein, E.H. et al., "Popsicle Panniculitis," The New England Journal of Medicine, 282(17):996-67, 1970.

(56) References Cited

OTHER PUBLICATIONS

European Search Report, European Patent Application No. 10167756.5, Applicant: The General Hospital Corporation, dated Aug. 31, 2010, 6 pages.
Final Office Action; U.S. Appl. No. 10/391,221; dated Aug. 24, 2006, 4 pages.
Final Office Action; U.S. Appl. No. 11/016,196; dated Mar. 23, 2010, 12 pages.
Final Office Action; U.S. Appl. No. 11/435,502; dated Mar. 29, 2010, 11 pages.
Final Office Action; U.S. Appl. No. 11/528,225; dated Dec. 29, 2010, 12 pages.
Final Office Action; U.S. Appl. No. 11/558,046; dated Mar. 30, 2011, 17 pages.
Gage, "Current Progress in Cryosurgery," Cryobiology 25, 483-486 (1988).
Hale et al., "Influence of chronic heat exposure and prolonged food deprivation on execretion of mahnesium, phosphorus, calcium, hydrogen ion & ketones," Aerosp Med, 1968, pp. 919-26, vol. 39—issue (9).
Heller-Page et al., "Temperature-dependent skin disorders," Journal of the American Academy of Dermatology, May 1988, vol. 18, No. 5, Pt 1, pp. 1003-1019.
Hemmingsson, "Attenuation in Human muscle and Fat Tissue in Vivo and in Vitro," Acta Radiologica Diagnosis 23, 149-151 (1982).
Henry et al., "Les Dermatoses Hivernales," Rev Med Liege, 1999, 54:11, 864-866. [Abstract Attached].
Holman, "Variation in cryolesion penetration due to probe size and tissue thermal conductivity," Ann. Thorac. Surg. 53, 123-126 (1992).
Hong, "Patterns of Ice Formulation in Normal and Malignant Breast Tissue," Cryobiology 31, 109-120 (1994).
International Search Report and Written Opinion for PCT/US2007/023492; Applicant: Zeltiq Aesthetics, Inc.; dated May 15, 2008, 7 pages.
International Search Report and Written Opinion for PCT/US2007/064016; Applicant: Juniper Medical, Inc.; dated Jul. 20, 2007, 13 pages.
International Search Report and Written Opinion for PCT/US2007/064017; Applicant: Juniper Medical, Inc.; dated Oct. 26, 2007, 16 pages.
International Search Report and Written Opinion for PCT/US2007/064018; Applicant: Juniper Medical, Inc.; dated Jul. 26, 2007, 13 pages.
International Search Report and Written Opinion for PCT/US2007/067638; Applicant: Juniper Medical, Inc.; dated Jan. 10, 2008, 11 pages.
International Search Report and Written Opinion for PCT/US2007/069694; Applicant: Juniper Medical, Inc.; dated Nov. 23, 2007, 12 pages.
International Search Report and Written Opinion for PCT/US2007/075935; Applicant: Zeltiq Aesthetics, Inc.; dated Apr. 10, 2008, 12 pages.
International Search Report and Written Opinion for PCT/US2007/083255; Applicant: Zeltiq Aesthetics, Inc.; dated Aug. 11, 2008, 8 pages.
International Search Report and Written Opinion for PCT/US2008/073930; Applicant: Zeltiq Aesthetics, Inc.; dated Nov. 7, 2008, 10 pages.
International Search Report and Written Opinion for PCT/US2007/062508; Applicant: Juniper Medical, Inc.; dated Jul. 20, 2007, 13 pages.
International Search Report and Written Opinion for PCT/US2009/058088; Applicant: Zeltiq Aesthetics, Inc.; dated Nov. 20, 2009, 14 pages.
International Search Report and Written Opinion for PCT/US2009/067973; Applicant: Zeltiq Aesthetics, Inc.; dated Feb. 18, 2010, 10 pages.
International Search Report for EP07758558.6; Applicant: Zeltiq Aesthetics, Inc.; dated Jul. 20, 2007, 4 pages.
International Search Report and Written Opinion for PCT/US2005/045988; Applicant: The General Hospital Corporation; dated Apr. 25, 2006, 14 pages.
International Search Report and Written Opinion for PCT/US2010/033290; Applicant: Zeltiq Aesthetics, Inc.; dated Feb. 25, 2011, 12 pages.
International Search Report and Written Opinion for PCT/US2011/022112; Applicant: Zeltiq Aesthetics, Inc.; dated Mar. 18, 2011, 11 pages.
International Search Report and Written Opinion for PCT/US2011/022444; Applicant: Zeltiq Aesthetics, Inc., dated Mar. 29, 2011, 14 pages.
Kellum, R.E. et al., "Sclerema Neonatorum: Report of Case and Analysis of Subcutaneous and Epidermal-Dermal Lipids by Chromatographic Methods," Arch. Derm., 97:372-80, 1968.
Koska, J. et al., "Endocrine Regulation of Subcutaneous Fat Metabolism During Cold Exposure in Humans," Ann N.Y. Acad, Sci., 967:500-05, 2002.
Kundu et al., "Breath acetone analyzer: diagnostic tool to monitor dietary fat loss," Clin Chem, 1993, pp. 87-92, vol. 39, issue (1).
Kundu et al., "Novel solid-phase assay of ketone bodies in urine," Clin Chem, 1991, pp. 15659, vol. 37—issue (9).
Kuroda et al., "Thermal distribution of radio-frequency inductive hyperthermia using an inductive aperture-type applicator: evaluation of the effect of tumour size and depth," Med Biol Eng Comput, 1999, pp. 285-90, vol. 37—issue (3).
Laugier, et al., "In Vivo Results with a New Device for Ultrasonic Monitoring of Pig Skin Cryosurgery: The Echographic Cryprobe," The society for Investigative Dermatology, Inc., vol. 111(2), Aug. 1998.
Levchenko, et al., "Effect of dehydration on lipid metabolism," WMJ, 1978, pp. 95-7, vol. 50—issue (1).
Lidagoster, MD et al., "Comparison of Autologous Fat Transfer in Fresh, Refridgerated, and Frozen Specimens: An Animal Model Presented," at the 16th Annual Meeting of the Northeastern Society of Plastic Surgeons: Burlington, VT, 1999, pp. 512-515.
Liu, A.Y.C. et al., "Transient Cold Shock Induces the Heat Shock Response upon Recovery at 37 C in Human Cells," J. Biol. Chem., May 20, 1994, 269(20), 14768-14775.
Lvova, "Lipid levels and lipid peroxidation in frog tissues during hypothermia and hibernation," WMJ, 1990, pp. 65-70, vol. 62—issue (1).
Maize, J.C., "Panniculitis," Cutaneous Pathology, Chapter 13:327-344, 1998.
Malcolm, G. et al., "Fatty Acid Composition of Adipose Tissue in Humans: Differences between Subcutaneous Sites," Am J Clin. Nutr., 50(2):288-91, 1989.
Merrill, Tom, "A Chill to the Heart: A System to Deliver Local Hypothermia Could One Day Improve the Lives of Heart-Attack Patients," Mechanical Engineering Magazine, Oct. 2010 (10 pages).
Moschella, S.L. et al., "Diseases of the Subcutaneous Tissue," Derm., Section 2:1169-1181, 1985.
Murphy, J.V. et al., "Frostbite: Pathogensis and Treatment," The Journal of Trauma: Injury, Infection, and Critical Care, 48(1):171-178, 2000.
Nagao et al., "Dietary diacylglycerol suppresses accumulation of body fat compared to triacylglycerol in men a double-blind controlled trial," J Nutr, 2000, pp. 792-7, vol. 130—issue (4).
Nagore et al., "Lipoatrophia semicircularis—a traumatic panniculitis: Report of seven cases and review of the literature," Journal of the American Academy of Dermatology, Nov. 1998, 39:879-81.
Nielsen, "Thermoregulation in Rest and Exercise," Acta Phys Scan Supp, 1969, pp. 6-74, vol. 323.
Nishikawa, "Ultrastructural Changes and Lipid Peroxidation in Rat Adipomusculocutaneous Flap Isotransplants after Normothermic Storage and Reperfusion," Transplantation, 1992, 54, 795-801.
Non-Final Office Action; U.S. Appl. No. 10/391,221; dated Jul. 22, 2005, 6 pages.
Non-Final Office Action; U.S. Appl. No. 10/391,221; dated Jan. 25, 2006, 6 pages.
Non-Final Office Action; U.S. Appl. No. 10/391,221; dated May 30, 2007, 8 pages.

(56) References Cited

OTHER PUBLICATIONS

Non-Final Office Action; U.S. Appl. No. 11/016,196; dated Sep. 25, 2009, 8 pages.
Non-Final Office Action; U.S. Appl. No. 11/016,196; dated Apr. 22, 2008, 11 pages.
Non-Final Office Action; U.S. Appl. No. 11/359,092; dated Nov. 19, 2009, 13 pages.
Non-Final Office Action; U.S. Appl. No. 11/435,502; dated Jul. 17, 2009, 10 pages.
Non-Final Office Action; U.S. Appl. No. 11/528,225; dated Apr. 12, 2010, 11 pages.
Non-Final Office Action; U.S. Appl. No. 11/558,046; dated Jul. 12, 2010, 14 pages.
Non-Final Office Action; U.S. Appl. No. 11/741,271; dated Jul. 12, 2010, 9 pages.
Non-Final Office Action; U.S. Appl. No. 12/942,852; dated Jun. 30, 2011, 10 pages.
Non-Final Office Action; U.S. Appl. No. 11/528,225; dated Aug. 3, 2011, 13 pages.
Non-Final Office Action; U.S. Appl. No. 12/565,613; dated Sep. 23, 2011, 55 pages.
Pease, "An Integrated Probe for Magnetic Resonance Imaging Monitored Skin Cryosurgery," Journal of Biomedical Engineering 117, 59-63, (1995).
Pech, "Attenuation values, volume changes and artifacts in tissue due to freezing," Acta Radiologica 6, 779-782 (1987).
Peterson et al., "Bilateral Fat Necrosis of the Scrotum, Urology Service, Department of Surgery, Dermatology Service, Department of Medicine and Department of Pediatrics," Letterman Army Medical Center, Journal of Urology, 1976, pp. 825-826, vol. 116, The Williams & Wilkins Co.
Phinney, S.D. et al., "Human Subcutaneous Adipose Tissue Shows Site-Specific Differences in Fatty Acid Composition," Am J. Clin. Nutr., 60:725-29, 1994.
Rabi, "Metabolic adaptations in brown adipose tissue of the hamster in extreme ambient temperatures," American Journal of Physiology 231, 153-160 (1976).
Renold, A.E., "Adipose Tissue," Handbook of Physiology, Chapter 15:170-76, 1965.
Rubinsky, "Cryosurgery: advances in the application of low temperatures to medicine," Int. J. Refrig. 190-199 (1991).
Schoning, et al., "Experimental Frostbite: Freezing Times, Rewarming Times, and Lowest Temperatures of Pig Skin Exposed to Chilled Air," Cryobiology, 1990, pp. 189-193, 27.
Shephard, "Adaptation to Exercise in the Cold," Sports Medicine, 1985, 2:59-71.
Wang et al., "Cryopreservation of cell/hydrogel constructs based on a new cell-assembling technique", Sep. 5, 2009, 40 pages.
Wharton et al., "Cold acclimation and cryoprotectants in a freeze-tolerant Antarctic nematode, Panagrolaimus davidi," Mar. 7, 2000, 2 pages.
Winkler et al., "Gene Transfer in Laboratory Fish: Model Organisms for the Analysis of Gene Function," Transgenic Animals, 1997, pp. 387-395.
Young, H.E. et al., "Isolation of Embryonic Chick Myosatellite and Pluripotent Stem Cells," J. Tiss. Cult. Meth., 14:85-92, 1992.
Aguilar et al., "Modeling Cryogenic Spray Temperature and Evaporation Rate Based on Single-Droplet Analysis", Eighth International Conference on Liquid Atomization and Spray Systems, Pasadena, CA, USA, Jul. 2000, 7 pages.
Alster, Tina et el. "Cellulite treatment using a novel combination radiofrequency, infrared light, and mechanical tissue manipulation device," J. of Cosmetic and Laser Therapy, vol. 7, 2005, p. 81-85.
Duck, Francis A., Physical Properties of Tissue, Academic Press Ltd., 1990, chapters 4 & 5, pp. 73-165.
Fournier, Luc et al. "Lattice model for the kinetics of rupture of fluid bilayer membranes," Physical Review, vol. 67, 2003, 051908-1-051908-11.
Gabriel, S. et al., "The dielectric properties of biological tissue: II. Measurements in the frequency range 10 Hz to 20 GHz," Phys. Medical Biology, vol. 41, 1996, p. 2251-2269.
Isambert, Herve "Understanding the Electroporation of Cells and Artificial Bilayer Membranes," Phys. Review Letters, vol. 80, 1998, pp. 3404-3707.
Saleh, K.Y. et el. "Two-dimensional ultrasound phased array design for tissue ablation for treatment of benign hyperplasia," Int. J. Hyperthermia, vol. 20, No. 1, Feb. 2004, p. 7-31.
Zouboulis et al., "Current Developments and Users of Cryosurgery in the Treatment of Keloids and Herpertrophic Scars", Wound Repair and Regeneration, vol. 10, No. 2, pp. 98-102, 2002.
Ardevol, et al., "Cooling Rates of Tissue Samples During Freezing with Liquid Nitrogen", Journal of Biochem and Biophysical Methods, 27, 1993, 77-86.
Peterson, et al., "Bilateral Fat Necrosis of the Scrotum", 116 Journal of Urology, 1976, 825-826.
Schoning, et al., "Experimental Frostbite: Freezing Times, Rewarming Times, and Lowest Temperatures of Pig Skin Exposed to Chilled Air", 27 Cryoboliogy, 1990, 189-193.
Hernan, P. et al., "Study for the evaluation of the efficacy of Lipocryolysis (EEEL)", Nov. 30, 2011.
Hernan, R. P., "A Study to Evaluate the Action of Lipocryolysis", 33(3) CryoLellers, 2012, pp. 176-180.
Jalian, H. R. et al., "Cryolipolysis: A Historical Perspective and Current Clinical Practice", 32(1) Semin. Cutan. Med. Surg., 2013, pp. 31-34.
Zelickson, B. et al., "Cryolipolysis for Noninvasive Fat Cell Destruction: Initial Results from a Pig Model", 35 Dermatol. Sug., 2009, pp. 1-9.

\* cited by examiner

DEVICES, APPLICATION SYSTEMS AND METHODS WITH LOCALIZED HEAT FLUX ZONES FOR REMOVING HEAT FROM SUBCUTANEOUS LIPID-RICH CELLS

CROSS-REFERENCE TO RELATED APPLICATION(S)

This application claims priority to U.S. Provisional Patent Application No. 61/435,944, filed Jan. 25, 2011, entitled "DEVICES, APPLICATION SYSTEMS AND METHODS WITH LOCALIZED HEAT FLUX ZONES FOR REMOVING HEAT FROM SUBCUTANEOUS LIPID-RICH CELLS," which is incorporated herein by reference in its entirety.

The following commonly-assigned U.S. Patent Applications are incorporated herein by reference in their entirety:

U.S. Patent Publication No. 2008/0287839 entitled "METHOD OF ENHANCED REMOVAL OF HEAT FROM SUBCUTANEOUS LIPID-RICH CELLS AND TREATMENT APPARATUS HAVING AN ACTUATOR";

U.S. Pat. No. 6,032,675 entitled "FREEZING METHOD FOR CONTROLLED REMOVAL OF FATTY TISSUE BY LIPOSUCTION";

U.S. Patent Publication No. 2007/0255362 entitled "CRYOPROTECTANT FOR USE WITH A TREATMENT DEVICE FOR IMPROVED COOLING OF SUBCUTANEOUS LIPID-RICH CELLS";

U.S. Pat. No. 7,854,754 entitled "COOLING DEVICE FOR REMOVING HEAT FROM SUBCUTANEOUS LIPID-RICH CELLS";

U.S. Patent Publication No. 2011/0066216 entitled "COOLING DEVICE FOR REMOVING HEAT FROM SUBCUTANEOUS LIPID-RICH CELLS";

U.S. Patent Publication No. 2008/0077201 entitled "COOLING DEVICES WITH FLEXIBLE SENSORS";

U.S. Patent Publication No. 2008/0077211 entitled "COOLING DEVICE HAVING A PLURALITY OF CONTROLLABLE COOLING ELEMENTS TO PROVIDE A PREDETERMINED COOLING PROFILE";

U.S. Patent Publication No. 2009/0118722, filed Oct. 31, 2007, entitled "METHOD AND APPARATUS FOR COOLING SUBCUTANEOUS LIPID-RICH CELLS OR TISSUE";

U.S. Patent Publication No. 2009/0018624 entitled "LIMITING USE OF DISPOSABLE SUBJECT 11 PROTECTION DEVICES";

U.S. Patent Publication No. 2009/0018623 entitled "SYSTEM FOR TREATING LIPID-RICH REGIONS";

U.S. Patent Publication No. 2009/0018625 entitled "MANAGING SYSTEM TEMPERATURE TO REMOVE HEAT FROM LIPID-RICH REGIONS";

U.S. Patent Publication No. 2009/0018627 entitled "SECURE SYSTEM FOR REMOVING HEAT FROM LIPID-RICH REGIONS";

U.S. Patent Publication No. 2009/0018626 entitled "USER INTERFACES FOR A SYSTEM THAT REMOVES HEAT FROM LIPID-RICH REGIONS";

U.S. Pat. No. 6,041,787 entitled "USE OF CRYOPROTECTIVE AGENT COMPOUNDS DURING CRYOSURGERY";

U.S. Patent Publication No. 2009/0149929 entitled "MONITORING THE COOLING OF SUBCUTANEOUS LIPID-RICH CELLS, SUCH AS THE COOLING OF ADIPOSE TISSUE";

U.S. Provisional Patent Application Ser. No. 60/941,567 entitled "METHODS, APPARATUSES AND SYSTEMS FOR COOLING THE SKIN AND SUBCUTANEOUS TISSUE";

U.S. Patent Publication No. 2010/0081971 entitled "TREATMENT PLANNING SYSTEMS AND METHODS FOR BODY CONTOURING APPLICATIONS";

U.S. patent application Ser. No. 12/275,002 entitled "APPARATUS WITH HYDROPHILIC RESERVOIRS FOR COOLING SUBCUTANEOUS LIPID-RICH CELLS";

U.S. patent application Ser. No. 12/275,014 entitled "APPARATUS WITH HYDROPHOBIC FILTERS FOR REMOVING HEAT FROM SUBCUTANEOUS LIPID-RICH CELLS";

U.S. Patent Publication No. 2010/0152824 entitled "SYSTEMS AND METHODS WITH INTERRUPT/RESUME CAPABILITIES FOR COOLING SUBCUTANEOUS LIPID-RICH CELLS";

U.S. Patent Publication No. 2008/0077202 entitled "TISSUE TREATMENT METHODS";

U.S. Patent Publication No. 2010/0280582 entitled "DEVICE, SYSTEM AND METHOD FOR REMOVING HEAT FROM SUBCUTANEOUS LIPID-RICH CELLS";

U.S. patent application Ser. No. 12/840,235 entitled "COMBINED MODALITY TREATMENT SYSTEMS, METHODS AND APPARATUS FOR BODY CONTOURING APPLICATIONS";

U.S. Publication No. 2011/0238050 entitled "HOME-USE APPLICATORS FOR NON-INVASIVELY REMOVING HEAT FROM SUBCUTANEOUS LIPID-RICH CELLS VIA PHASE CHANGE COOLANTS, AND ASSOCIATED DEVICES, SYSTEMS AND METHODS"; and U.S. Publication No. 2011/0238051 entitled "HOME-USE APPLICATORS FOR NON-INVASIVELY REMOVING HEAT FROM SUBCUTANEOUS LIPID-RICH CELLS VIA PHASE CHANGE COOLANTS, AND ASSOCIATED DEVICES, SYSTEMS AND METHODS".

TECHNICAL FIELD

The present application relates generally to devices, application systems and methods for removing heat from subcutaneous lipid-rich cells. In particular, several embodiments are directed toward a device that provides independent control of the heat flux through a plurality of zones based on a desired heat flux profile.

BACKGROUND

Excess body fat, or adipose tissue, may be present in various locations of the body, including, for example, the thigh, buttocks, abdomen, knees, back, face, arms, chin, and other areas. Moreover, excess adipose tissue is thought to magnify the unattractive appearance of cellulite, which forms when subcutaneous fat protrudes into the dermis and creates dimples where the skin is attached to underlying structural fibrous strands. Cellulite and excessive amounts of adipose tissue are often considered to be unappealing. Moreover, significant health risks may be associated with higher amounts of excess body fat.

A variety of methods have been used to treat individuals having excess body fat and, in many instances, non-invasive removal of excess subcutaneous adipose tissue can eliminate unnecessary recovery time and discomfort associated with invasive procedures such as liposuction. Conventional non-invasive treatments for removing excess body fat typically include topical agents, weight-loss drugs, regular exercise, dieting or a combination of these treatments. One drawback of these treatments is that they may not be effective or even possible under certain circumstances. For example, when a person is physically injured or ill, regular exercise may not be an option. Similarly, weight-loss drugs or topical agents are not an option when they cause an allergic or negative reaction. Furthermore, fat loss in selective areas of a person's body often cannot be achieved using general or systemic weight-loss methods.

Other methods designed to reduce subcutaneous adipose tissue include laser-assisted liposuction and mesotherapy. Newer non-invasive methods include applying radiant energy to subcutaneous lipid-rich cells via, e.g., radio frequency and/or light energy, such as described in U.S. Patent Publication No. 2006/0036300 and U.S. Pat. No. 5,143,063, or via, e.g., high intensity focused ultrasound (HIFU) radiation such as described in U.S. Pat. Nos. 7,258,674 and 7,347,855. In contrast, methods and devices for non-invasively reducing subcutaneous adipose tissue by cooling are disclosed in U.S. Pat. No. 7,367,341 entitled "METHODS AND DEVICES FOR SELECTIVE DISRUPTION OF FATTY TISSUE BY CONTROLLED COOLING" to Anderson et al. and U.S. Patent Publication No. 2005/0251120 entitled "METHODS AND DEVICES FOR DETECTION AND CONTROL OF SELECTIVE DISRUPTION OF FATTY TISSUE BY CONTROLLED COOLING" to Anderson et al., the entire disclosures of which are incorporated herein by reference.

BRIEF DESCRIPTION OF THE DRAWINGS

In the drawings, identical reference numbers identify similar elements or acts. The sizes and relative positions of elements in the drawings are not necessarily drawn to scale. For example, the shapes of various elements and angles are not necessarily drawn to scale, and some of these elements are arbitrarily enlarged and positioned to improve drawing legibility. Further, the particular shapes of the elements as drawn are not necessarily intended to convey any information regarding the actual shape of the particular elements, and are generally selected for ease of recognition in the drawings.

DETAILED DESCRIPTION

Overview

Figure 1:
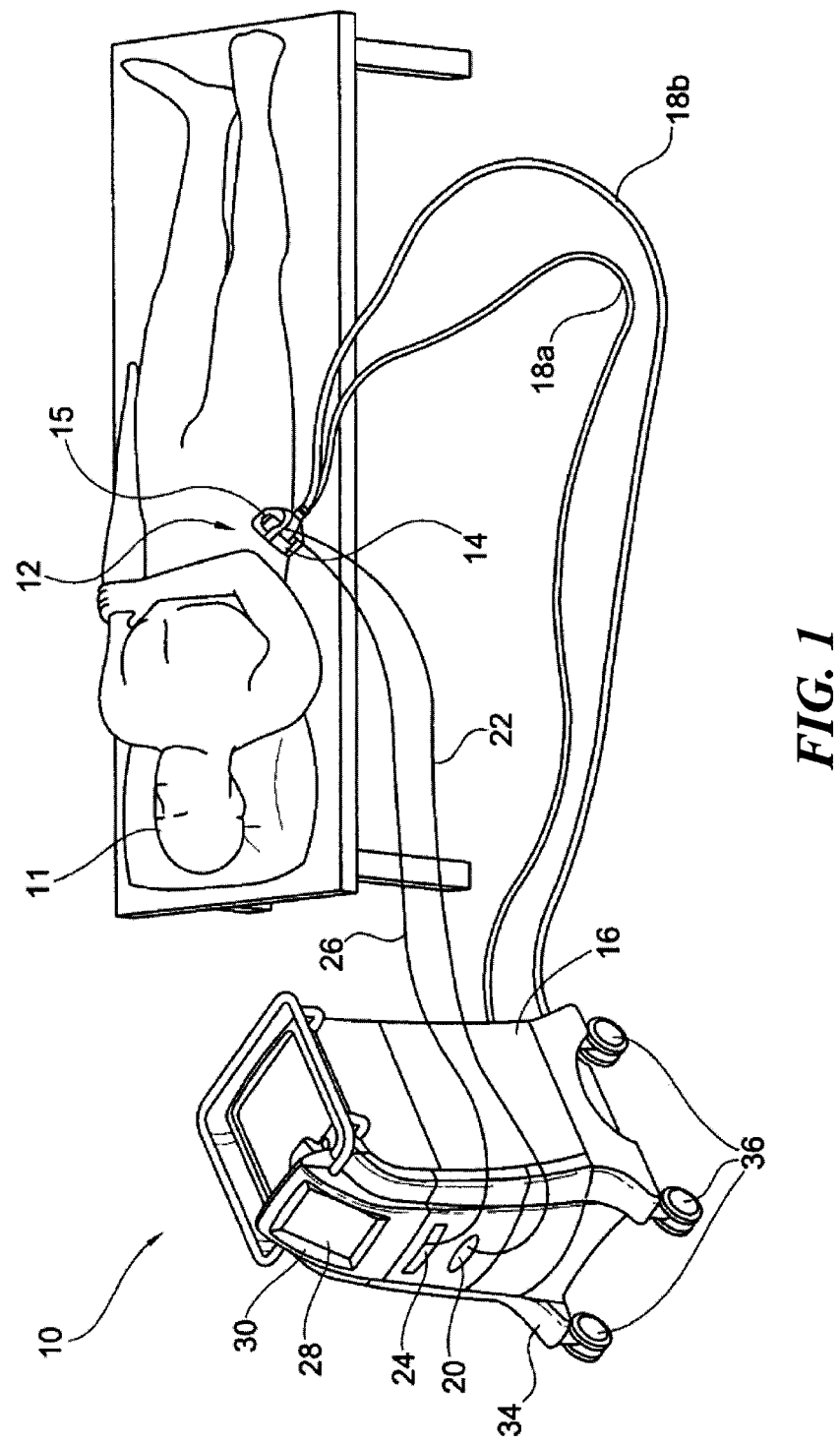
FIG. 1 is an isometric view schematically illustrating a treatment system for treating subcutaneous lipid-rich regions of a subject in accordance with an embodiment of the technology.

Several examples of devices, application systems and methods for independently controlling the heat flux through a plurality of cooling zones for cooling subcutaneous adipose tissue in accordance with the technology are described below. Although the following description provides many specific details of the following examples in a manner sufficient to enable a person skilled in the relevant art to practice, make and use them, several of the details and advantages described below may not be necessary to practice certain examples and methods of the technology. Additionally, the technology may include other examples and methods that are within the scope of the claims but are not described in detail.

Reference throughout this specification to "one example," "an example," "one embodiment" or "an embodiment" means that a particular feature, structure, or characteristic described in connection with the example is included in at least one example of the present technology. Thus, the occurrences of the phrases "in one example," "in an example," "one embodiment" or "an embodiment" in various places throughout this specification are not necessarily all referring to the same example. Furthermore, the particular features, structures, routines, steps or characteristics may be combined in any suitable manner in one or more examples of the technology. The headings provided herein are for convenience only and are not intended to limit or interpret the scope or meaning of the claimed technology.

One embodiment of an application system for cooling subcutaneous lipid-rich tissue comprises a cooling unit, a cryoprotectant vessel, a contact member and an array of selectably addressable heating elements. The cryoprotectant vessel is configured to contain a fluidic cryoprotectant such that at least a portion of the cryoprotectant is cooled by the cooling unit to a desired base temperature. The contact member is attached to the cryoprotectant vessel, and the contact member includes a backside in contact with the cryoprotectant and a front side opposite the backside. The contact member is configured to allow the cryoprotectant to flow from the backside to the front side, and the array of selectably addressable heating elements is carried by the contact member.

One embodiment of a method of operating an application system for cooling subcutaneous lipid-rich tissue includes cooling a cryoprotectant to a base temperature below 37° C. The method further includes passing the cyroprotectant through a flexible contact member of an interface element, and selectively heating at least one heating element of an array of heating elements carried by the flexible contact member to a temperature different than other heating elements of the array. As a result, the temperature of the cryoprotectant proximate to the heated heating element is raised to a contact temperature higher than the base temperature.

In a more detailed embodiment of an application system for cooling subcutaneous lipid-rich tissue, the cooling unit comprises a heat exchanger having a coolant chamber through which a coolant can flow. The cryoprotectant vessel comprises a back panel and a sidewall projecting from the back panel. The contact member is a flexible barrier attached to the sidewall of the cryoprotectant vessel to form a cryoprotectant chamber, and the flexible barrier and the cryoprotectant vessel together form a disposable interface element. The flexible barrier, for example, can be a porous membrane or other flexible panel with small holes. The interface assembly further comprises a connector that couples the cryoprotectant vessel to the cooling unit. The application system of this embodiment further comprises an array of temperature sensor sets carried by the flexible membrane, and each individual heating element is associated with a corresponding temperature sensor set. Additionally, the application system can optionally comprise a larger heating element spaced apart from the backside of the array of temperature sensor sets and a controller. The controller includes a computer-operable medium programmed to receive sensed temperatures from the temperature sensor sets and adjust the associated heating elements based on the sensed temperatures and a desired heating profile to thereby provide localized temperature differentials in the cryoprotectant corresponding to the desired heating profile.

General System Components

FIG. 1 and the following discussion provide a brief, general description of a suitable treatment system 10 in which aspects of the present technology can be implemented. Those skilled in the relevant art will appreciate that the present technology can be practiced with other systems and treatment protocols, including invasive, minimally invasive, other non-invasive cosmetic or medical treatment systems and/or combinations of one or more of the above for treating a subject 11. In general, the term "treatment system", as used generally herein, refers to any of the above system categories of cosmetic or medical treatments as well as any treatment regimes or medical device usage.

The treatment system 10 is suitable for cooling the subcutaneous adipose tissue of a subject 11 in a manner that reduces the volume of the adipose tissue. "Subcutaneous tissue" can include tissue lying beneath the dermis and includes subcutaneous fat, or adipose tissue that may be composed primarily of lipid-rich cells, or adipocytes. When cooling subcutaneous tissues to a temperature lower than 37° C., subcutaneous lipid-rich cells can be affected selectively. In general, the epidermis and dermis of the subject 11 lack lipid-rich cells compared to the underlying lipid-rich cells forming the adipose tissue. Because non-lipid-rich cells usually can withstand colder temperatures better than lipid-rich cells, the subcutaneous lipid-rich cells can be affected selectively without affecting the non-lipid-rich cells in the dermis, epidermis and other surrounding tissue. In some embodiments, the treatment system 100 can apply cooling temperatures to the skin of the subject 11 in a range of about −20° C. to about 20° C. In other embodiments, the cooling temperatures can be from about −20° C. to about 10° C., approximately 0° C. to approximately 20° C., about −15° C. to about 5° C., approximately −5° C. to approximately 15° C., or about −10° C. to about 0° C.

Without being bound by theory, the selective effect of cooling on lipid-rich cells is believed to result in, for example, membrane disruption, cell shrinkage, disabling, destroying, removing, killing or other methods of lipid-rich cell alteration. Such alteration is believed to stem from one or more mechanisms acting alone or in combination. It is thought that such mechanism(s) trigger an apoptotic cascade, which is believed to be the dominant form of lipid-rich cell death by non-invasive cooling.

Apoptosis, also referred to as "programmed cell death", is a genetically-induced death mechanism by which cells self-destruct without incurring damage to surrounding tissues. An ordered series of biochemical events induce cells to morphologically change. These changes include cellular blebbing, loss of cell membrane asymmetry and attachment, cell shrinkage, chromatin condensation and chromosomal DNA fragmentation. Injury via an external stimulus, such as cold exposure, is one mechanism that can induce cellular apoptosis in cells. Nagle, W. A., Soloff, B. L., Moss, A. J. Jr., Henle, K. J. "Cultured Chinese Hamster Cells Undergo Apoptosis After Exposure to Cold but Nonfreezing Temperatures" *Cryobiology* 27, 439-451 (1990).

One aspect of apoptosis, in contrast to cellular necrosis (a traumatic form of cell death causing local inflammation), is that apoptotic cells express and display phagocytic markers on the surface of the cell membrane, thus marking the cells for phagocytosis by macrophages. As a result, phagocytes can engulf and remove the dying cells (e.g., the lipid-rich cells) without eliciting an immune response. Temperatures that elicit these apoptotic events in lipid-rich cells may contribute to long-lasting and/or permanent reduction and reshaping of subcutaneous adipose tissue.

One mechanism of apoptotic lipid-rich cell death by cooling is believed to involve localized crystallization of lipids within the adipocytes at temperatures that do not induce crystallization in non-lipid-rich cells. The crystallized lipids selectively may injure these cells, inducing apoptosis (and may also induce necrotic death if the crystallized lipids damage or rupture the bi-lipid membrane of the adipocyte). Another mechanism of injury involves the lipid phase transition of those lipids within the cell's bi-lipid membrane, which results in membrane disruption, thereby inducing apoptosis. This mechanism is well-documented for many cell types and may be active when adipocytes, or lipid-rich cells, are cooled. Mazur, P., "Cryobiology: the Freezing of Biological Systems" Science, 68: 939-949 (1970); Quinn, P. J., "A Lipid Phase Separation Model of Low Temperature Damage to Biological Membranes" Cryobiology, 22: 128-147 (1985); Rubinsky, B., "Principles of Low Temperature Preservation" *Heart Failure Reviews,* 8, 277-284 (2003). Other yet-to-be understood apoptotic mechanisms may exist, based on the relative sensitivity of lipid-rich cells to cooling compared to non-lipid rich cells.

In addition to the apoptotic mechanisms involved in lipid-rich cell death, local cold exposure also is believed to induce lipolysis (i.e., fat metabolism) of lipid-rich cells and has been shown to enhance existing lipolysis which serves to further increase the reduction in subcutaneous lipid-rich cells. Vallerand, A. L., Zamecnik. J., Jones, P. J. H., Jacobs, I. "Cold Stress Increases Lipolysis, FFA Ra and TG/FFA Cycling in Humans" *Aviation, Space and Environmental Medicine* 70, 42-50 (1999).

In various embodiments, the treatment system 10 includes a controller, a computing device, a data acquisition device, a chiller, and one or more treatment devices. These components can be implemented in various embodiments to apply selected treatment profiles to a subject 11 (e.g., a human or animal) for reducing adipose tissue.

FIG. 1 is a perspective view illustrating one example of a treatment system 10 for non-invasively removing heat from subcutaneous lipid-rich target areas of the subject 11, such as an abdominal area 12 or another suitable area. The system 10 may include a treatment device 14 that engages the target area of the subject 11 and a treatment unit 16 that operate together to cool or otherwise remove heat from the subcutaneous lipid-rich cells of the subject 11. The treatment devices 14 can be part of an application system, and the treatment device 14 can have various, configurations, shapes and sizes suitable for different body parts such that heat can be removed from any subcutaneous lipid-rich target area of the subject 11. For example, the treatment devices 14 may be designed to treat target areas of the patient's body, such as chin, cheeks, arms, pectoral areas, thighs, calves, buttocks, back, abdomen, "love handles" and so forth. The treatment devices 14 can have a cooling unit 15 that cools a selected area of the subject 11. As explained in more detail below, the system 10 can also include a disposable protective device and a cryoprotect for cooling the lipid-rich adipose tissue.

In the embodiment illustrated in FIG. 1, the treatment device 14 may provide mechanical energy to create a vibratory, massage and/or pulsatile effect in addition to cooling subcutaneous adipose tissue, such as the devices described in U.S. Pat. No. 7,367,341 and commonly assigned U.S. Patent Publication No. 2008/0287839. The treatment device 14, for example, may include one or more actuators that generate a transitory force which is transmitted to the subject. Suitable actuators include motors with eccentric weights, hydraulic motors, electric motors, pneumatic motors, solenoids, other mechanical motors, piezoelectric shakers and other devices that provide vibratory energy to the treatment site. A single treatment device 14 may have a plurality of different types of actuators in any desired combination. For example, the treatment device 14 may have an eccentric weight actuator (not shown) and a pneumatic motor (not shown) such that different effects may be provided with the same treatment device 14. This would provide a number of options for differential treatments of lipid rich cells within a single target area or among multiple target areas of subject 11.

The cooling unit 15 can be a component of a cooling unit integrated with the treatment device 14, and the cooling unit 15 may include one or more Peltier-type thermoelectric elements, such as a plurality of individually controlled thermal segments that create a custom spatial cooling profile and/or a time-varying cooling profile. Each custom treatment profile can include one or more segments, and each segment can include a specified duration, a target temperature, and control parameters for features such as vibration, massage, vacuum and other treatment modes. Cooling devices having multiple individually controlled heat exchanging units are described, e.g., in commonly assigned U.S. Patent Publication No. 2008/0077211.

The treatment unit 16 may be a refrigeration unit, a cooling tower, a thermoelectric chiller or cooler or any other device or cooling unit capable of removing heat from a coolant in addition to or in lieu of the cooling unit 15 at the treatment device. The treatment unit 16 can be operatively coupled to the treatment device 14 by supply and return fluid lines 18a and 18b that circulate chilled fluid (e.g., a coolant) through the treatment device 14. Alternatively, the treatment unit 16 can circulate warm fluid to the treatment device 14 during periods of warming. Examples of the circulating coolant include water, glycol, synthetic heat transfer fluid, oil, a refrigerant, a cryoprotectant and/or any other suitable heat-conducting fluid. The fluid lines 18a and 18b may be hoses or other conduits constructed from polyethylene, polyvinyl chloride, polyurethane and/or other materials that can accommodate the particular circulating coolant. Furthermore, one skilled in the art will recognize that there are a number of other cooling technologies that could be used such that the cooling units or coolers of the treatment unit 16 or the treatment device 14 need not be limited to those described herein.

The system 10 may further include a power supply 20 and a processing unit 24 operatively coupled to the treatment device 14, the cooling unit 15 and/or the treatment unit 16. In one example, the power supply 20 provides a direct current voltage to a thermoelectric element of the cooling unit 15 to adjust the heat flux over a relatively large area. The processing unit 24 may monitor process parameters via sensors (not shown) placed proximate to the treatment device 14 through power line 26 to, among other things, adjust the heat removal rate based on the process parameters. The processing unit 24 may further monitor process parameters to adjust the cooling unit 15 or other components based on the process parameters.

The processing unit 24 may be in direct electrical communication with treatment device 14 through the electrical line 22 as shown in FIG. 1; alternatively, processing unit 24 may be connected to treatment device via a wireless or an optical communication link. For example, the processing unit 24 may be in electrical communication with a control panel of the treatment device 14, the cooling unit 15 and/or an interface assembly. The processing unit 24 may be any processor, programmable logic controller, distributed control system and so on. Although the power line 26 and the electrical line 22 are shown in FIG. 1 without any support structure, these lines and other lines including, but not limited to the fluid lines 18a and 18b, may be bundled into or otherwise accompanied by a conduit or the like to protect the lines, enhance user safety and ergonomic comfort, inhibit unwanted motion that could adversely impact the heat transfer rate, provide electrical and thermal insulation and provide an aesthetic appearance to the system 10. Examples of such a conduit include a flexible polymeric fabric, a composite sheath, an adjustable arm, etc. Such a conduit (not shown) may be designed (via adjustable joints, etc.) to "set" the conduit in place for the treatment of the subject 11.

Figure 3:
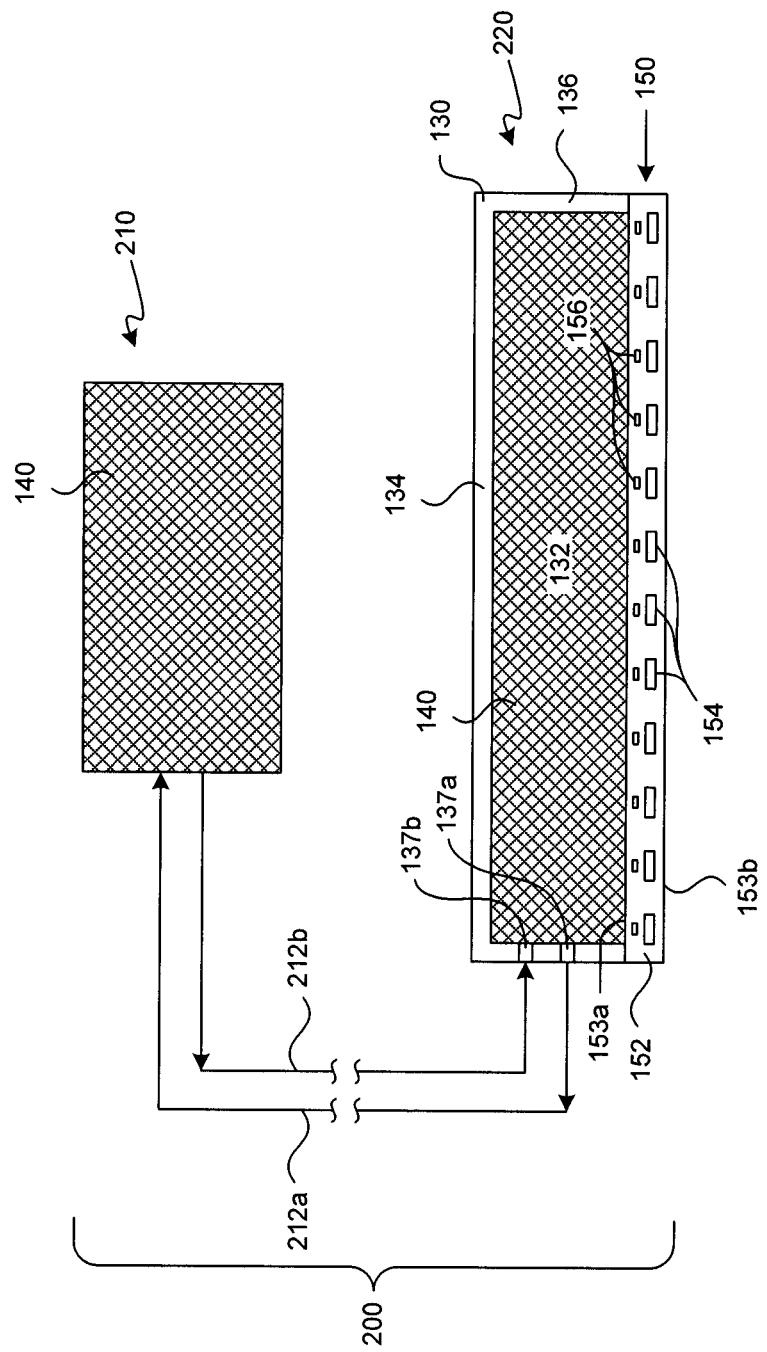
FIG. 3 is a schematic cross-sectional view of an application system for cooling subcutaneous lipid-rich tissue in accordance with an embodiment of the technology.

The system 10 can also include an input device 28 and an output device 30 operatively coupled to the processing unit 24. The input device 28 may be a keyboard (shown in FIG. 1), a mouse, a touch screen, a push button, a switch, a potentiometer, any combination thereof and any other device or devices suitable for accepting user input. The output device 30 may include a display or touch screen, a printer, a medium reader, an audio device, a visual device, any combination thereof and any other device or devices suitable for providing user feedback. In the embodiment of FIG. 1, the input device 28 and the output device 30 may be combined in a single unit such as a touch screen. The control panel 14b may include visual indicator devices or controls (lights, numerical displays, etc.) and/or audio indicator devices or controls. The control panel of the treatment device 14 may be a separate component from the input device and/or output device as shown in FIG. 3, or the control panel may be (a) integrated with one or more of the input and output devices 28 and 30, (b) partially integrated with one or more of the input and output devices 28 and 30, (c) at another location, and so on. In this example, the processing unit 24, the power supply 20, the treatment unit 16, the input device 28 and the output device 30 are carried by a rack or cart 34 with wheels 36 for portability. In alternative examples, the processing unit 24 may be contained in, attached to, or integrated with the treatment device 14, the cooling unit 15 and/or an interface assembly. In yet another example, the various components may be fixedly installed at a treatment site. Further details with respect to selected versions of the components and/or operation of the treatment device 14, cooling unit 15 and other components may be found in commonly-assigned U.S. Patent Publication No. 2008/0287839.

Without being bound by theory, it is believed that effective conductive cooling from the treatment device 14 depends on a number of factors. Examples of factors that impact heat removal or extraction from the skin and related tissue include, for example, the surface area of the treatment unit, the temperature of the interface member, the mechanical energy delivered to the tissue, the distribution of cryoprotectant and the extent of non-uniformities in the contact between the interface member and the skin. More specifically, upon receiving input to start a treatment protocol, the processing unit 24 can cause the treatment device 14 to cycle through each segment of a prescribed treatment plan. In so doing, the treatment device 14 applies power to one or more cooling segments, such as thermoelectric coolers (e.g., TEC "zones"), to begin a cooling cycle and, for example, activate features or modes such as vibration, massage, vacuum, etc. Using temperature or heat flux sensors, the processing unit 24 determines whether the temperature and/or heat flux at one or more areas of the actuator are sufficiently close to a target temperature or target heat flux. It will be appreciated that while a region of the body (e.g., adipose tissue) has been cooled or heated to the target temperature or by a target heat flux, in actuality that region of the body may be close but not equal to the target temperature, e.g., because of the body's natural heating and cooling variations. Thus, although the system may attempt to heat or cool to the target temperature or by a target heat flux, a sensor may measure a sufficiently close temperature. If the target temperature has not been reached, power can be increased or decreased to change heat flux, as needed, to maintain the target temperature or "setpoint." When the prescribed segment duration expires, the processing unit 24 may apply the temperature and duration indicated in the next treatment profile segment. In some embodiments, temperature can be controlled using a variable other than, or in addition to, power.

A cryoprotectant is used with the treatment device 14. Among other advantages, a cryoprotectant can assist in preventing freezing of non lipid-rich tissue (e.g., dermal tissue) during treatment. Suitable cryoprotectants and processes for implementing cryoprotectants are described in commonly-assigned U.S. Patent Publication No. 2007/0255362 and U.S. patent application Ser. No. 13/011,640 filed on Jan. 21, 2011, which are hereby incorporated by reference. As used herein, "cryoprotectant" means a flowable compound that prolongs the time to freeze non lipid-rich tissue (e.g., dermal tissue) compared to an absence of the compound.

In one example of operating the system 10, the treatment device 14 is drawn against the skin of the subject 11 to achieve efficient treatment. The subject 11 generally has a body temperature of about 37° C., which is maintained at a relatively constant level by circulation of blood. As a result, blood flow through the skin and subcutaneous layer of the region to be treated acts as a heat source that counteracts the cooling of the subdermal fat. Cooling the tissue of interest accordingly requires not only removing the heat from the target tissue but also from the blood circulating through this tissue. The efficiency of cooling the tissue can be enhanced by temporarily reducing or eliminating blood flow through the treatment region using a vacuum or other technique. Applying a vacuum may also pull skin and underlying adipose tissue away from the body which can assist in cooling underlying tissue by increasing the distance between the subcutaneous fat and the relatively well-perfused muscle tissue and by allowing the underlying adipose tissue simultaneously to be cooled from two sides.

By cooling the subcutaneous tissue to a temperature lower than 37° C., subcutaneous lipid-rich cells may be damaged selectively. In general, the epidermis and dermis of the subject 11 have lower amounts of fatty acids compared to the underlying lipid-rich cells forming the subcutaneous tissues. Because non-lipid-rich cells usually can withstand colder temperatures better than lipid-rich cells, the subcutaneous lipid-rich cells can be injured selectively while maintaining the non-lipid-rich cells in the dermis and epidermis. The presence of a cryoprotectant at and/or on the dermal tissue enhances the selectivity such that the dermal tissue can withstand even colder temperatures which induce cell death in more lipid-rich tissue. For example, the temperature range may be from about −10° C. to about 0° C.

Several embodiments of the system 10 may damage, injure, disrupt or otherwise reduce subcutaneous lipid-rich cells generally without collateral damage to non-lipid-rich cells in the treatment target area. In general, it is believed that lipid-rich cells can be affected selectively (e.g., damaged, injured or disrupted) by exposing such cells to low temperatures that do not adversely affect non-lipid-rich cells to the same extent or in the same manner. As a result, lipid-rich cells, such as subcutaneous adipose tissue, can be damaged while other cells in the same region are generally not damaged even though the non-lipid-rich cells at the surface are subject to even lower temperatures. The mechanical energy provided by the applicator may further enhance the effect on lipid-rich cells by mechanically disrupting the affected lipid-rich cells.

Figure 2A:
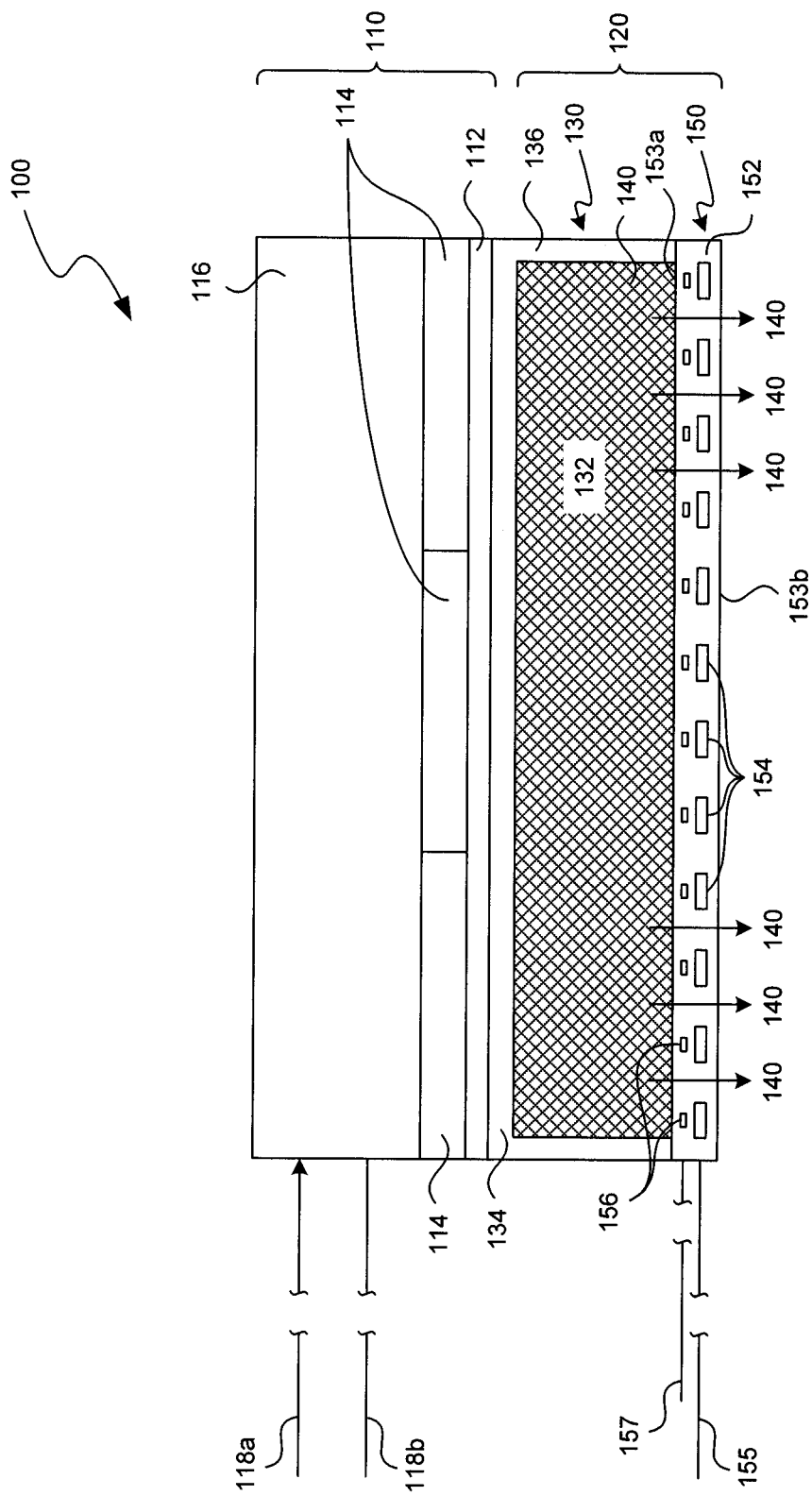
FIG. 2A is a schematic cross-sectional view of an application system for cooling subcutaneous lipid-rich tissue in accordance with an embodiment of the technology.

FIG. 2A is a schematic cross-sectional view of an application system 100 for cooling subcutaneous lipid-rich tissue. The application system 100, for example, may include a treatment device and a cooling unit integrated with the treatment device and/or with the treatment unit. In this embodiment, the application system 100 is a treatment device configured to contact the target area. The application system 100 can include a cooling unit 110 and an interface assembly 120 operably coupled to the cooling unit 110. The cooling unit 110, for example, may be similar to the cooling unit 15 of the treatment device 14 described above with reference to FIG. 1. The embodiment of the cooling unit 110 shown on FIG. 2A can include a plate 112 that has a high thermal conductivity, one or more Thermoelectric Elements (TEEs) 114 and a coolant chamber 116. As explained above with reference to FIG. 1, a coolant can recirculate through the coolant chamber 116 via inlet and outlet lines 118a and 118b, respectively, and the TEEs 114 can selectively heat and/or cool relative to the temperature of the coolant in the coolant chamber 116 to control the temperature over relatively large areas of the cooling plate 112. Other embodiments of the cooling unit 110 do not include the TEEs 114 such that the coolant chamber 116 extends to the cold plate 112. In either case the cooling unit 110 provides a heat sink that cools the interface assembly 120.

The interface assembly 120 further controls the heat flux through a plurality of smaller zones and delivers a cryoprotectant to the target area. In one embodiment, the interface assembly 120 includes a cryoprotectant container 130 having a cavity 132 that contains a cryoprotectant 140 and an interface element 150 through which the cryoprotectant 140 can flow. The cryoprotectant container 130 can be a rigid or flexible vessel having a back panel 134 facing the cooling unit 110 and a sidewall 136 projecting from the back panel 134. The interface element 150 can be attached to the sidewall 136 to enclose the cavity 132. The interface element 150 can include a contact member 152 having a backside 153a in contact with the cryoprotectant 140 and a front side 153b configured to contact the epidermis of the subject. The contact member 152 can be a flexible barrier (e.g., membrane) such as a porous sheet of a polymeric material or a foil with small holes, a mesh, fabric or other suitable material through which the cryoprotectant 140 can flow from the backside 153a to the front side 153b. In other embodiments, the contact member 152 can be a substantially rigid barrier that is thermally conductive and configured to allow the cryoprotectant 140 to pass from the front side 153b to the backside 153a. A rigid contact member, for example, can be a plate with holes or a panel made from a porous metal material. Suitable materials for a rigid contact member 152 include aluminum, titanium, stainless steel, or other thermally conductive materials.

The interface element 150 of the application system 100 further includes an array of heating elements 154 carried by the contact member 152. The individual heating elements 154 can be arranged in a grid or other type of pattern, and each heating element 154 is independently controlled relative to the other heating elements to provide control of the heat flux through smaller, discrete zones at the interface between the target area and the interface element 150. The heating elements 154, for example, can be micro-heaters electrically coupled to a power source via a cable 155 such that the controller can selectably address individual heating elements 154. The interface element 150 can further include a plurality of temperature sensors 156 carried by the contact member 152. The temperature sensors 156 may be arranged in an array such that one or more temperature sensors can measure the heat flux through the heat flux zones associated with one or more individual heating elements 154. The temperature sensors 156 can be electrically coupled to a control unit via a cable 157 in a manner similar to the heating elements 154.

Figure 2B:
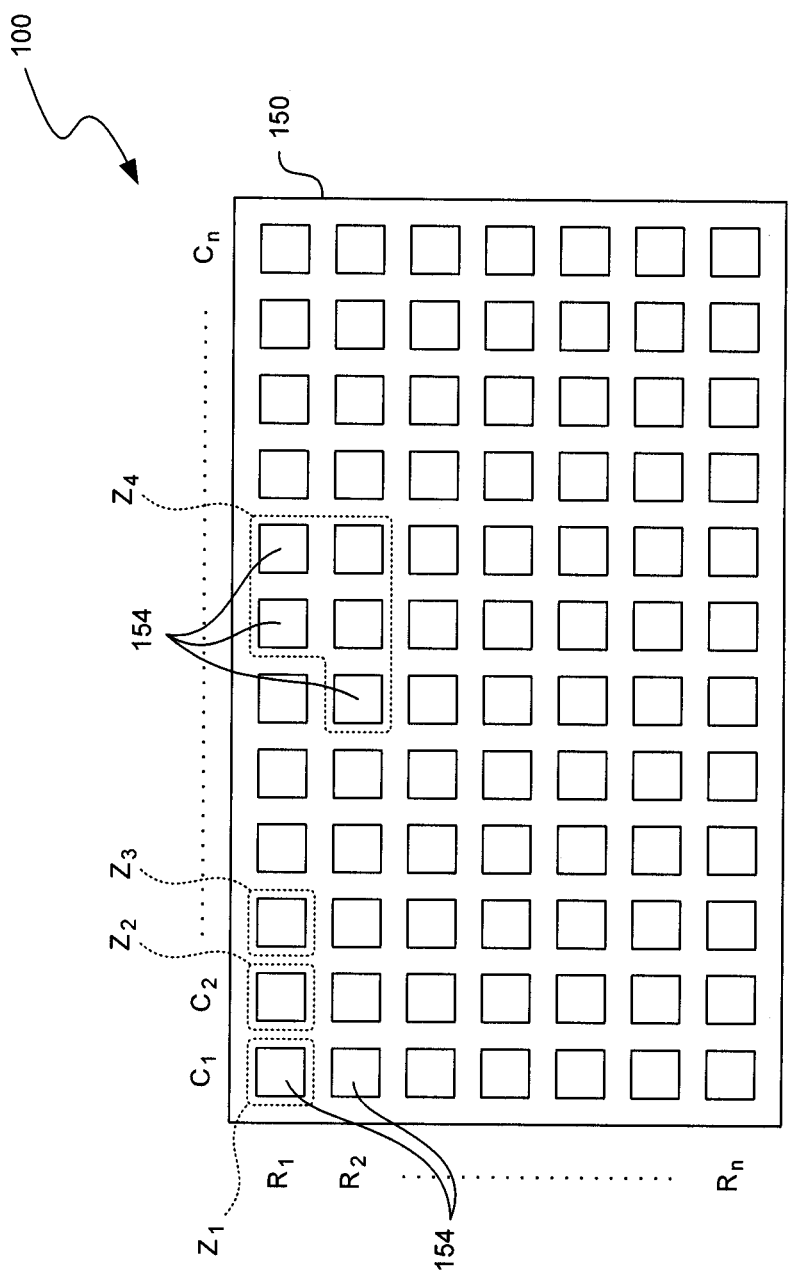
FIG. 2B is a schematic bottom view of an interface assembly of an application system for cooling subcutaneous lipid-rich tissue in accordance with an embodiment of the technology.

FIG. 2B is a schematic bottom view of the interface element 150. Referring to FIGS. 2A and 2B together, the heating elements 154 can be arranged in a grid having $C_1$-$C_n$ columns and $R_1$-$R_n$ rows. Each individual heating element 154 can define a heat flux zone Z through which the heat flux can be selectively controlled relative to other areas of the interface element 150 (see, e.g., heat flux zones $Z_1$, $Z_2$ and $Z_3$). In other embodiments, a plurality of heating elements 154 can be grouped together into a set that defines a heat flux zone (see, e.g., heat flux zone $Z_4$). In other embodiments, the heating elements 154 can be arranged in different configurations. The temperature sensors 156 can also be arranged in the same grid as the heating elements 154. For example, each column-row address can have one or more temperature sensors 156 to measure the temperature and/or heat flux associated with each individual heating element 154 or heat flux zone.

The cable 155 (FIG. 2A) can include a plurality of individual wires that electrically couple corresponding individual heating elements 154 to a multi-channel power source. The cable 157 (FIG. 2A) can similarly include individual wires that electrically couple the temperature sensors 156 to an analog-to-digital converter, which is then coupled to a controller. In operation, the controller can operate the power source to selectively address the independent heating elements 154 based upon the column and row to provide a desired cooling profile in the subcutaneous lipid-rich tissue.

In operation, a target site of the subject is registered relative to the grid of heating elements of the interface element 150. The target site can have a single heat flux zone, or the target site can be divided into a number of different areas in which each area is associated with a corresponding heat flux zone. In either situation, a practitioner inputs the extent of desired cooling for the heat flux zones or this information can be provided to the controller by a predetermined control algorithm. The interface element 150 is positioned at the target site of the subject. In many applications, the interface element 150 and the epidermis of the target site are coapted under pressure provided by a vacuum, belt or other mechanism that forces the skin of the subject against the interface element 150. The cryoprotectant 140 in the cryoprotectant container 130 flows through the interface element 150 and contacts the skin of the subject, and a coolant is recirculated through the coolant chamber 116 of the cooling unit 110 to globally cool the back panel 134 of the cryoprotectant container 130.

The temperature at the back panel 134 can be optionally controlled regionally using TEEs 114. The cooling provided by the cooling unit 110 reduces the temperature of the cryoprotectant 140 in the cryoprotectant container 130 to a base temperature. While the interface element 150 contacts the target site, a controller selectively activates the heating elements 154 to control the heat flux through the heat flux zones across the target site. The temperature and/or heat flux at the individual heat flux zones across the target site can be monitored via the temperature sensors 156 to provide closed loop control of the heat flux according to the predetermined algorithm. Suitable algorithms for defining and controlling the heat flux are disclosed in U.S. Patent Publication No. 2010/0152824 (U.S. patent application Ser. No. 12/337,544), which is herby incorporated by reference.

Several embodiments of the application assembly 100 enhance the control of the heat flux across different regions of the target area. This can be useful because different subjects may have different deposits of lipid-rich tissue within a target area, or the subject may have particularly sensitive dermal tissue at particular regions of the target area. Moreover, the enhanced control of the heat flux through the individual heat flux zones enables more accurate control of the cooling profile within the lipid-rich tissue.

FIG. 3 is a schematic illustration of an application system 200 for cooling subcutaneous lipid-rich tissue in accordance with another embodiment of the technology. Like reference numbers refer to similar components in FIGS. 2A-3. The embodiment of the application system 200 shown in FIG. 3 includes a cooling unit 210 and treatment device having an interface assembly 220 located remotely from the cooling unit 210. For example, the cooling unit 210 can be a cooler or chiller in the treatment unit 16 located in the rack or cart 34 shown in FIG. 1. In this particular embodiment, the cryoprotectant vessel 130 further includes outlet/inlet ports 137a and 137b, respectively, and the application system 200 further includes recirculation lines 212a and 212b extending between the cooling unit 210 and the interface assembly 220. In operation, the cooling unit 210 cools and recirculates the cryoprotectant 140 through the recirculation lines 212a-b and the cavity 132 of the cryoprotectant container 130. The cryoprotectant 140 flows through the contact member 152, and the heating elements 154 control the heat flux through the heat flux zones as described above with reference to FIGS. 2A and 2B. The application system 200 of this embodiment accordingly cools the cryoprotectant remotely from the interface assembly 220. As such, the cooling unit 220 and recirculation lines 212a-b can be flushed or cleaned between treating different subjects, and/or the cryoprotectant 140 can include a germicide.

Figure 4:
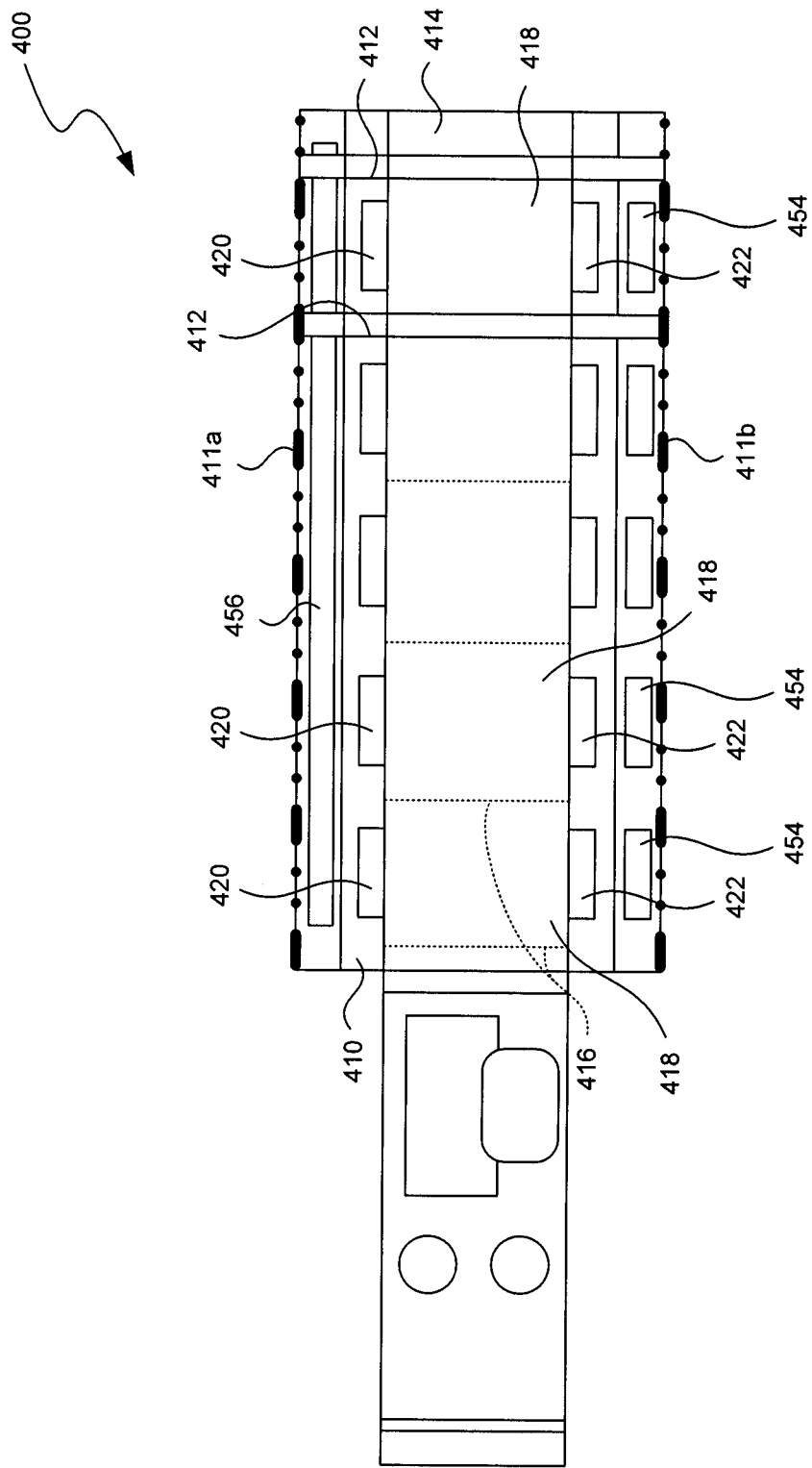
FIG. 4 is a schematic cross-sectional view of an interface element of an interface assembly for cooling subcutaneous lipid-rich tissue in accordance with an embodiment of the technology.

FIG. 4 is a schematic cross-sectional view of another embodiment of an interface element 400 for use in the application assembly 100 for cooling subcutaneous lipid-rich tissue. In this embodiment, the interface element 400 includes a flexible barrier 410 having a backside 411a, a front side 411b opposite the backside 411a and a plurality of channels 412 or other structure through which the cryoprotectant can pass from the backside 411a to the front side 411b (e.g., a porous structure). The interface element 400 further includes a thermal gradient layer 414 having a known thickness, thermal conductivity and heat capacity. The thermal gradient layer 414 has a plurality of striations 416 or other types of discontinuities that divide the thermal gradient layer 414 into a plurality of heat flux units 418. The interface element 400 further includes a set of temperature sensors having a dorsal temperature sensor 420 and a ventral temperature sensor 422 associated with each heat flux unit 418. The dorsal temperature sensors 420 indicate the temperature of the thermal gradient layer 414 toward the backside 411a of the barrier 410, and the ventral temperature sensors 422 indicate the temperature of the thermal gradient layer 414 toward the skin of the subject. The heat flux through each heat flux unit 418 can be determined based upon the difference between the dorsal and ventral temperature sensors 420 and 422 in combination with the known thickness, thermal conductivity and heat capacity of the thermal gradient layer 414.

The embodiment of the interface element 400 shown in FIG. 4 further includes a plurality of heating elements 454. More specifically, the interface element 400 can include one or more heating element 454 associated with individual heat flux units 418. The interface element 400 can optionally include a backside heating element 456 at the backside 411a of the barrier 410. The backside heating element 456 can globally heat the cryoprotectant at the backside 411a to provide a desired known temperature uniformly across the backside 411a. In operation, the cooling unit (not shown in FIG. 4) is set to a base temperature and the backside heating element 456 is adjusted to provide the desired backside temperature of the cryoprotectant. This enables quick and accurate adjustment of the set point for the cryoprotectant entering the interface element 400. The heating elements 454 are then controlled to provide the desired heat flux through the individual heat flux units 418. As described above, a heat flux zone can be defined by a single heat flux unit 418, or a set of heat flux units 418 can define a heat flux zone.

Figure 5A:
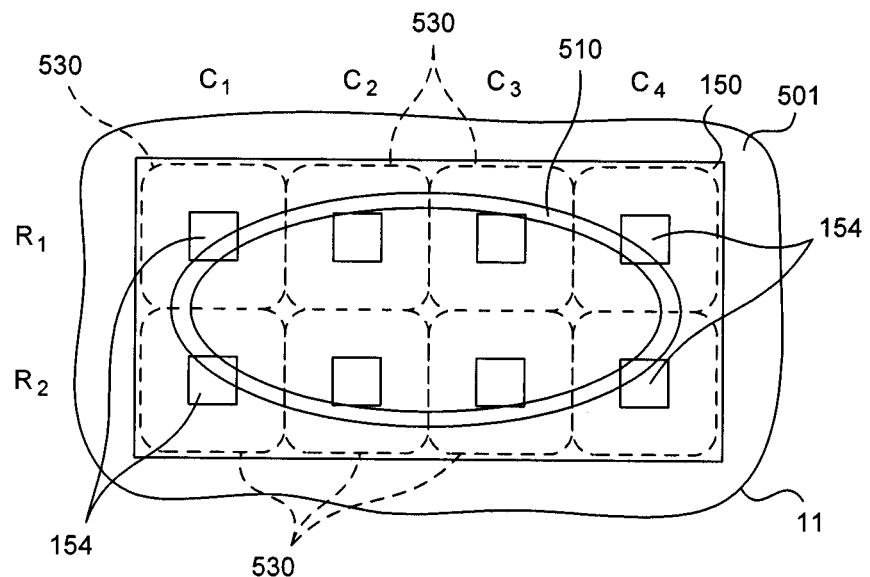
FIGS. 5A and 5B are schematic views of an implementation of an application system for cooling subcutaneous lipid-rich tissue in accordance with an embodiment of the technology.
Figure 5B:
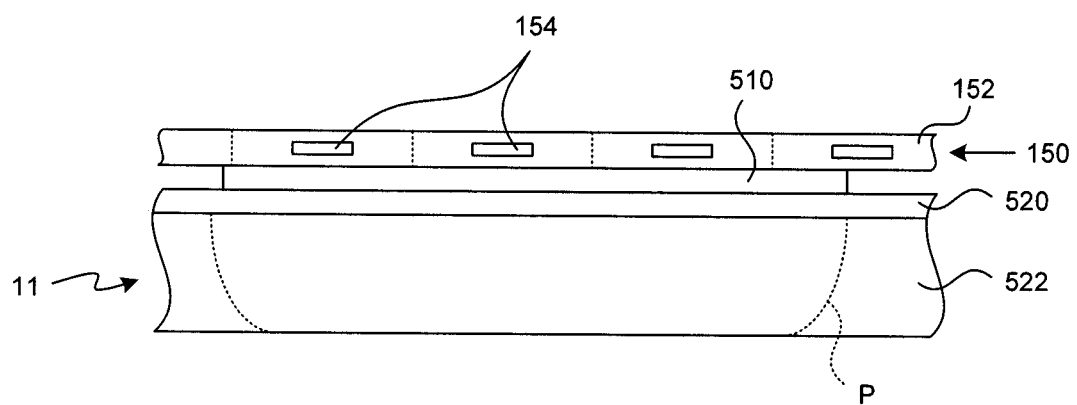

FIGS. 5A and 5B illustrate another implementation of application assemblies for cooling subcutaneous lipid-rich tissue in accordance with the technology. In this embodiment, one or more markers 510 are placed on the skin 520 of the subject 11 such that the markers 510 define the perimeter of the target area. The interface assembly 120 is positioned so that a number of the heating elements 154 are superimposed over the region defined by the markers 510. The heating elements 154 are then controlled based upon the outline of the target area defined by the markers 510 and the desired heat flux through the various heat flux zones 530. In the illustrated embodiment, for example, the heat flux through the heat flux zones 530 associated with columns $C_2$ and $C_3$ can be greater than that through the corresponding heat flux zones 530 associated with columns $C_1$ and $C_4$. This can be achieved by providing more heat to the heating elements in columns $C_1$ and $C_4$ compared to those in columns $C_2$ and $C_3$ and/or the smaller surface areas defined by the markers 510 in columns $C_1$ and $C_4$. Referring to FIG. 5B, this provides a controlled treatment profile P that extends through the skin 520 and into the lipid-rich tissue 522 for reducing the volume of the lipid-rich tissue as described above.

The markers 510 can be conductive members or dielectric templates. In one example, the markers 510 are a conductive ink or magnetic ink that is deposited on the skin 520 of the patient around the perimeter of the treatment area. The heating elements 154 can include sensors that detect the presence of the inks, and the controller can then selectively operate the heating elements based on the outline of the markers 510. In another example, the markers 510 are defined by a dielectric template that has an opening in the shape of the treatment area. The heating elements 154 can be operated to focus the heat flux through the opening of the template. For example, the heating elements 154 can sense the heat flux through the corresponding heat flux zones, and the controller can determine the shape of the opening based on a greater heat flux through the opening compared to areas covered by the dielectric material.

Figure 6:
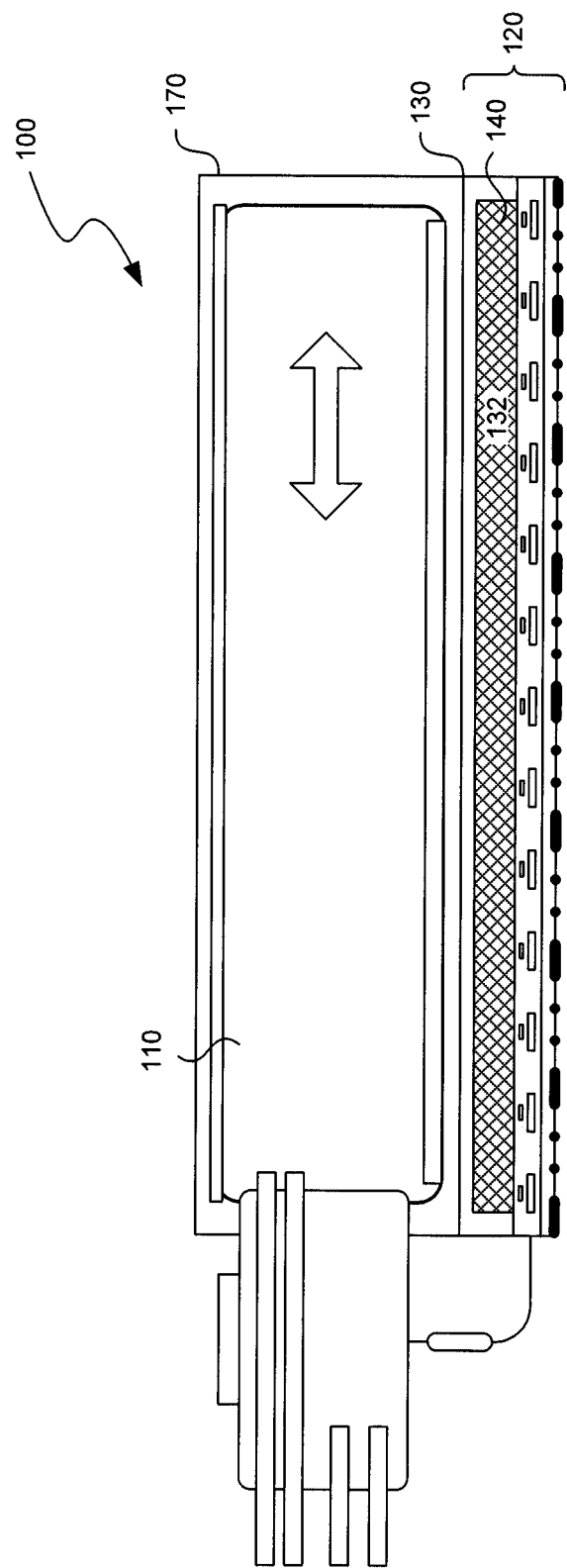
FIG. 6 is a schematic cross-sectional view of an application system for cooling subcutaneous lipid-rich tissue in accordance with an embodiment of the technology.

FIG. 6 is a schematic cross-sectional view of another embodiment of the application system. In this embodiment, the interface assembly 120 further includes a connector 170 that couples the cryoprotectant vessel 130 to the cooling unit 110. The connector 170 can comprise a sheath or pocket in which cooling unit 110 is received to treat a subject. After performing the treatment, the interface assembly 120 can be removed and disposed appropriately. The cooling unit 110 can then be inserted into a new, sterile interface assembly for treating the next subject.

Figure 7:
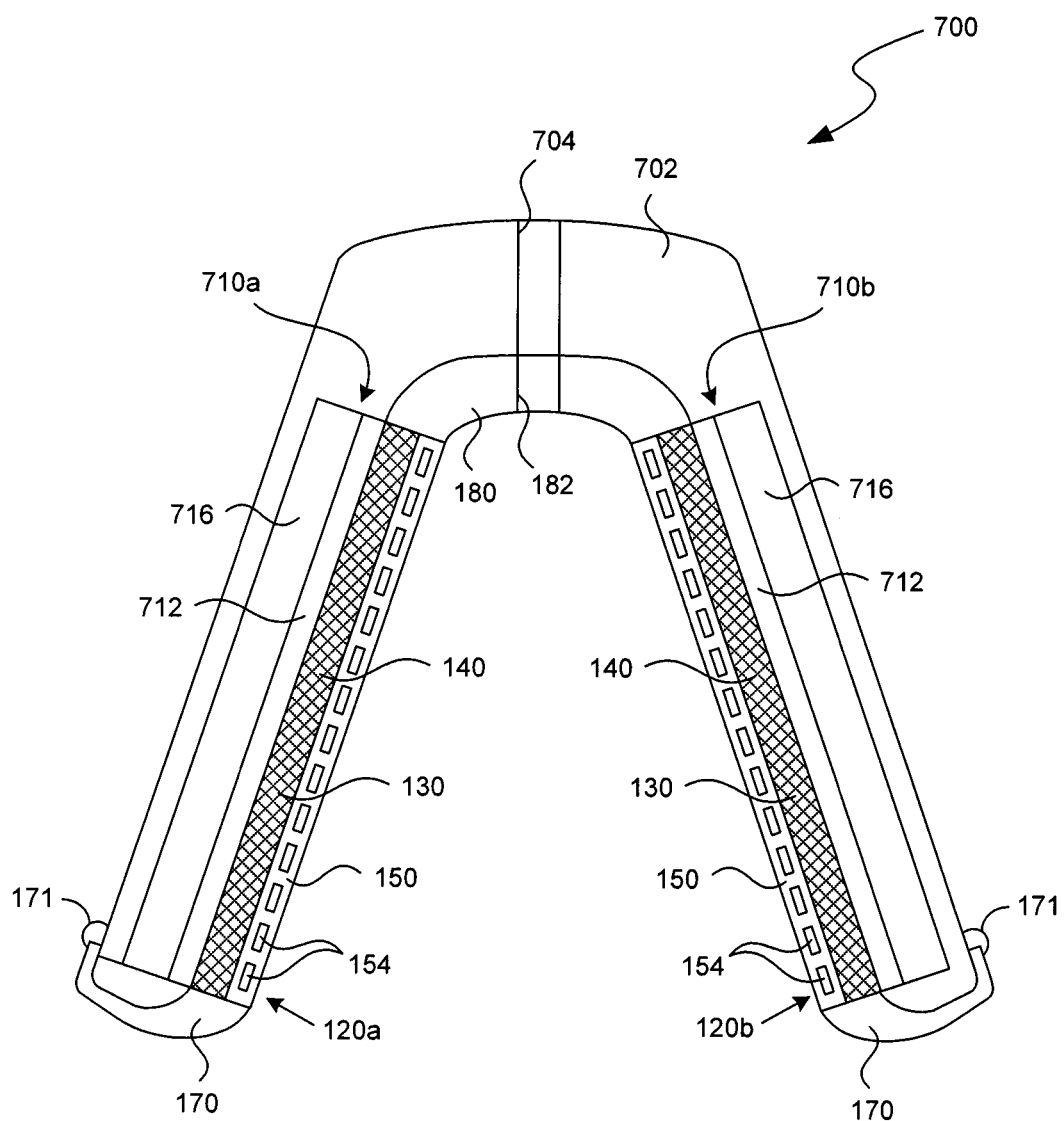
FIG. 7 is a schematic cross-sectional view of a treatment device with an application system for cooling subcutaneous lipid-rich tissue in accordance with an embodiment of the technology.

FIG. 7 is a schematic cross-sectional view of an application system 700 for cooling lipid-rich tissue in accordance with another embodiment of the technology. The treatment device 700 includes a vacuum cup 702 having a vacuum port 704, a first cooling unit 710a on one side of the cup 702, and a second cooling unit 710b on an opposing side of the cup 702. Each of the first and second cooling units 710a and 710b can be similar to the cooling unit 110 described above with reference to FIGS. 2A and 2B. As such, each of the cooling units 710a-b can include a cold plate 712 and a coolant chamber 716. The cooling units 710a-b can be fixed to the vacuum cup 702.

In this embodiment, the treatment device 700 also includes a first interface assembly 120a and a second interface assembly 120b within the vacuum cup 702. More specifically, the first interface assembly 120a is adjacent the first cooling unit 710a and the second interface assembly 120b is adjacent the second cooling unit 710b. The first and second interface assemblies 120a-b can further include connectors 170 in the form of tabs or other mechanisms that can be secured by clasps or clamps 171 to releasably attach the first and second interface assemblies 120a-b to the vacuum cup 702. The first and second interface assemblies 120a-b can also be connected to each other by a flexible intermediate portion 180. The intermediate portion 180 can include a vacuum port 182 aligned with the vacuum port 704 of the vacuum cup 702, or the intermediate portion 180 can have a porous through which air can flow. In operation, the rim of the vacuum cup is placed against the skin of a subject and a vacuum is drawn within the cup. The vacuum pulls the tissue of the subject into the cup 702 and coapts the target area with the interface elements 150 of the corresponding first and second interface assemblies 120a-b. One suitable vacuum cup 702 with cooling units is described in U.S. Provisional Patent Application Ser. No. 61/174,407, filed on Apr. 30, 2009, and incorporative by reference above.

From the foregoing, it will be appreciated that specific embodiments of the invention have been described herein for purposes of illustration, but that various modifications may be made without deviating from the spirit and scope of the invention. The application systems, interface assemblies and methods may be combined in further embodiments. For example, the interface element 400 shown and described with reference to FIG. 4 can be used in any of the interface assemblies 120, 120*a-b* or 200 described above with reference to FIGS. 2A-3 and 5A-7. In addition, while advantages associated with certain embodiments have been described and the context of those embodiments, other embodiments may also exhibit such advantages. Not all embodiments need necessarily exhibit such advantages to fall within the scope of the present disclosure. Accordingly, the invention is not limited except as by the appended claims.

We claim:

1. An application system for cooling subcutaneous lipid-rich tissue, comprising: a cooling unit; a cryoprotectant vessel configured to contain a cryoprotectant such that at least a portion of the cryoprotectant is cooled by the cooling unit to a desired cold temperature; a contact member configured to be attached to the cryoprotectant vessel, the contact member including a backside configured to contact the cryoprotectant and a front side opposite the backside and a thermal gradient layer having one or more physical discontinuities configured to define one or more units of the thermal gradient layer, wherein each unit is associated with one or more of a plurality of selectably addressable heating elements; an array of the plurality of selectably addressable heating elements carried by the contact member, and wherein the contact member is configured to allow the cryoprotectant to flow from the backside to the front side; and a controller with a stored profile and being programmed to cause the application system to cool the subcutaneous lipid-rich tissue, and command one or more heating elements of the array of selectably addressable heating elements to warm the subcutaneous lipid-rich tissue, which has been cooled by the application system, based on the stored profile while the application system cools the subcutaneous lipid-rich tissue to disrupt subcutaneous lipid-rich cells, wherein the stored profile includes a target heat flux profile, a target temperature profile, or a combination thereof.

2. The application system of claim 1,
wherein the cooling unit comprises a heat exchanger having a coolant chamber through which a coolant can flow;
wherein the cryoprotectant vessel comprises a backpanel and a sidewall projecting from the backpanel, the contact member is a flexible barrier attached to the sidewall of the cryoprotectant vessel to form a cryoprotectant chamber, the flexible barrier and the cryoprotectant vessel together form an interface assembly, and the interface assembly further comprises a connector coupling the cryoprotectant vessel to the cooling unit;
the application system further comprising an array of temperature sensor sets carried by the flexible barrier, wherein individual heating elements of the array of selectably addressable heating elements are associated with corresponding temperature sensor set of the array of temperature sensor sets;
the application system further comprising an additional heating element positioned to heat the cryoprotectant contained in the cryoprotectant vessel, the additional heating element being spaced apart from the array of temperature sensor sets; and
the application system further comprising a controller including a computer-operable medium programmed to receive sensed temperatures from the temperature sensor sets and adjust the associated individual heating elements of the array of selectably addressable heating elements based on the sensed temperatures and a desired heating profile, thereby providing localized temperature differentials in the cryoprotectant corresponding to the desired heating profile.

3. The application system of claim 1, wherein the cooling unit comprises a cold plate and a heat exchanger having a coolant chamber through which a coolant can flow, and wherein the heat exchanger is in thermal communication with the cold plate.

4. The application system of claim 3, wherein the cooling unit further comprises at least one thermoelectric element between the cold plate and the heat exchanger.

5. The application system of claim 1, wherein the contact member is a flexible barrier attached to the cryoprotectant vessel such that the flexible barrier and the cryoprotectant vessel together form an interface element.

6. The application system of claim 5, wherein the interface element further comprises a connector coupling the cryoprotectant vessel to the cooling unit.

7. The application system of claim 6, wherein the connector comprises a sheath associated with the cryoprotectant vessel, and the cooling unit is received within the sheath.

8. The application system of claim 7 wherein the sheath and the cryoprotectant vessel are integrally formed together such that the sheath extends from the cryoprotectant vessel.

9. The application system of claim 6 wherein the connector comprises a tab extending from the cryoprotectant vessel, and wherein the application system includes a clasp configured to releasably hold the tab.

10. The application system of claim 1, wherein the cryoprotectant vessel comprises a backpanel facing the cooling unit and a sidewall projecting from the backpanel, and wherein the contact member is a flexible barrier attached to the sidewall of the cryoprotectant vessel to form a cryoprotectant chamber.

11. The application system of claim 10, wherein the interface assembly further comprises a pad containing a cryoprotectant gel in the cryoprotectant chamber.

12. The application system of claim 10, wherein the cryoprotectant vessel further comprises an inlet into the cryoprotectant chamber and an outlet from the cryoprotectant chamber such that cryoprotectant can flow through the cryoprotectant chamber.

13. The application system of claim 1, wherein the cryoprotectant vessel further comprises an inlet and an outlet configured to direct a flow of the cryoprotectant through the cryoprotectant vessel.

14. The application system of claim 13, wherein:
the cryoprotectant vessel comprises a backpanel, a sidewall projecting from the backpanel, an inlet and an outlet;
the contact member is a flexible barrier attached to the sidewall of the cryoprotectant vessel to form a cryoprotectant chamber, wherein the inlet and outlet of the cryoprotectant vessel are configured to direct a flow of liquid cryoprotectant through the cryoprotectant chamber; and
the cooling unit comprises a cold plate and a heat exchanger having a coolant chamber through which a coolant can flow, and wherein the cold plate is in contact with the backpanel of the cryoprotectant vessel.

15. The application system of claim 13, wherein:
the cryoprotectant vessel comprises a backpanel, a sidewall projecting from the backpanel, an inlet, an outlet, and a conduit having one portion connected to the inlet and another portion connected to the outlet;

the contact member is a flexible barrier attached to the sidewall of the cryoprotectant vessel to form a cryoprotectant chamber, wherein the inlet and the outlet of the cryoprotectant vessel are configured to direct a flow of liquid cryoprotectant through the cryoprotectant chamber; and the cooling unit is spaced apart from the cryoprotectant chamber and coupled to the conduit, and wherein the cooling unit cools the flow of liquid cryoprotectant.

16. The application system of claim 1, wherein the array of selectably addressable heating elements is arranged in a grid, and individual heating elements of the array of selectably addressable heating elements can be independently controlled from each other.

17. The application system of claim 16, further comprising an array of temperature sensors carried by the contact member, wherein individual heating elements of the array of selectably addressable heating elements are associated with at least one corresponding temperature sensor.

18. The application system of claim 16, further comprising an array of temperature sensor sets carried by the contact member, wherein individual heating elements of the array of selectably addressable heating elements are associated with a corresponding temperature sensor set.

19. The application system of claim 1, wherein the cooling unit comprises a backside heating element in thermal communication with the contact member.

20. The application system of claim 1 wherein the array of selectably addressable heating elements is located directly between a chamber for holding the cryoprotectant and the front side of the contact member.

21. The application system of claim 1 wherein the array of selectably addressable heating elements is configured and positioned to heat the subject's skin.

22. The application system of claim 1, wherein the controller is programmed to adjust an amount of heat generated by one or more heating elements of the array of selectable heating elements while the cooling unit operates to cool the subcutaneous lipid-rich tissue so as to produce a heat flux profile or a temperature profile along the front side of the contact member sufficiently close to a target heat flux profile or a target temperature profile.

23. An application assembly for cooling subcutaneous lipid-rich tissue, comprising: a cooling unit; a disposable interface assembly having a connector configured to retain the disposable interface assembly in contact with the cooling unit, a cryoprotectant vessel proximate the cooling unit such that a cryoprotectant is cooled to a desired base temperature, and an interface element having a contact member through which the cryoprotectant can pass, wherein the contact member includes a thermal gradient interface having one or more physical discontinuities configured to define one or more units of the thermal gradient interface, wherein each unit is associated with one of a plurality of selectably addressable heating elements arranged into an array and carried by the contact member; and a controller including a computer-operable medium programmed to cause the cooling unit to operate to cool subcutaneous lipid-rich tissue to disrupt subcutaneous lipid-rich cells and to cause one or more heating elements of the array of addressable heating elements to warm tissue while the cooling unit cools the subcutaneous lipid-rich tissue.

24. A disposable interface assembly for an application system that cools subcutaneous lipid-rich tissue, comprising a cryoprotectant container having a cavity and an interface element enclosing one side of the cavity, wherein the interface element includes a flexible contact member and an array of selectably addressable heating elements carried by the flexible contact member, wherein the contact member includes a thermal gradient layer having one or more physical discontinuities configured to define one or more units of the thermal gradient layer, wherein each unit is associated with each of the selectably addressable heating elements and wherein the flexible contact member is configured to allow a cryoprotectant to flow through the flexible contact member.

25. The disposable interface assembly of claim 24, further comprising a flowable cryoprotectant gel in the cavity.

26. The disposable interface assembly of claim 24, further comprising a connector attached to the cryoprotectant container, wherein the connector is configured to retain the cryoprotectant container proximate to a cooling unit.

27. The disposable interface assembly of claim 24, wherein the array of selectably addressable heating elements is positioned between the cavity and a patient-facing surface of the flexible contact and operable to warm a first region of tissue cooled by the application system while the applicator system cools a second region of tissue in contact with cryoprotectant that been delivered through the contact member.

28. An application system for cooling subcutaneous lipid-rich tissue, comprising: a cooling unit; a cryoprotectant vessel configured to contain a cryoprotectant such that at least a portion of the cryoprotectant is cooled by the cooling unit to a desired cold temperature; a contact member including a backside positioned to contact the cryoprotectant in the cryoprotectant vessel and a front side opposite the backside, a thermal gradient layer having one or more physical discontinuities configured to define one or more units of the thermal gradient layer, wherein each unit is associated with one of a plurality of selectably addressable heating elements, and, wherein the contact member is configured to allow the cryoprotectant to flow from the backside to the front side; and wherein the selectably addressable heating elements are positioned between the cryoprotectant in the cryoprotectant vessel and the front side of the contact member; and a controller programmed to cause the cooling unit to operate to cool the subcutaneous lipid-rich tissue and programmed to independently control the selectably addressable heating elements to adjust an amount of heat generated by one or more of the selectably addressable heating elements to warm tissue cooled by the application system while the cooling unit operates to cool the subcutaneous lipid-rich tissue so as to produce a heat flux profile, a temperature profile, or a combination thereof along the front side of the contact member based on a target heat flux profile, a target temperature profile, or a combination thereof.

29. The application system of claim 28, further comprising temperature sensors for monitoring operation of each of the selectably addressable heating elements, and wherein each of the temperature sensors is positioned directly between a respective one of the selectably addressable heating elements and a surface of the contact member at the front side of the contact member.

30. An application system for cooling subcutaneous lipid-rich tissue, comprising: a cooling unit; a cryoprotectant vessel configured to contain a cryoprotectant such that at least a portion of the cryoprotectant is cooled by the cooling unit to a desired cold temperature; a contact member configured to be attached to the cryoprotectant vessel, the contact member including a backside configured to contact the cryoprotectant and a front side opposite the backside and a thermal gradient layer having one or more physical discontinuities configured to define one or more units of the thermal gradient layer, wherein each unit is associated with one of a plurality of selectably addressable heating elements, an array of the plurality of selectably addressable heating elements carried by the contact member, and wherein the contact member is configured to allow the cryoprotectant to flow from the backside to the front side; and a controller with a stored profile and being programmed to cause the application system to cool the subcutaneous lipid-rich tissue, and command one or more heating elements of the array of selectably addressable heating elements to warm tissue, which has been cooled by the application system, based on the stored profile while the application system cools the subcutaneous lipid-rich tissue to disrupt subcutaneous lipid-rich cells, wherein the stored profile includes a target heat flux profile, a target temperature profile, or a combination thereof.

31. An application system for cooling subcutaneous lipid-rich tissue, comprising: a cooling unit having a contact member, the contact member having a thermal gradient layer including one or more physical discontinuities configured to define one or more thermal units in the thermal gradient layer, a plurality of selectably addressable heating elements carried by the contact member, wherein each thermal unit is associated with one or more of the selectably addressable heating elements; a cryoprotectant in contact with the contact member such that the cryoprotectant is cooled by the cooling unit to a desired cold temperature; and a controller with a stored profile and being programmed to cause the application system to cool the subcutaneous lipid-rich tissue, and command one or more heating elements of the array of selectably addressable heating elements to warm the subcutaneous lipid-rich tissue adjacent to the heating elements, which tissue has been cooled by the application system, based on the stored profile while the application system cools the subcutaneous lipid-rich tissue to disrupt subcutaneous lipid-rich cells, wherein the stored profile includes a target heat flux profile, a target temperature profile, or a combination thereof.

32. The application system of claim 31, wherein the physical discontinuities and the selectably addressable heating elements define discrete heating regions along the cooling unit.

* * * * *